(12) United States Patent
Park et al.

(10) Patent No.: US 10,537,391 B2
(45) Date of Patent: Jan. 21, 2020

(54) TOTAL HIP REPLACEMENT SURGICAL GUIDE TOOL

(71) Applicant: Howmedica Osteonics Corporation, Mahwah, NJ (US)

(72) Inventors: Ilwhan Park, Walnut Creek, CA (US); Michael Koehle, Oakland, CA (US); Lorenzo R. Deveza, Houston, TX (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 183 days.

(21) Appl. No.: 15/875,895

(22) Filed: Jan. 19, 2018

(65) Prior Publication Data

US 2018/0140358 A1 May 24, 2018

Related U.S. Application Data

(60) Continuation of application No. 15/202,417, filed on Jul. 5, 2016, now Pat. No. 9,901,404, which is a
(Continued)

(51) Int. Cl.
*A61B 34/10* (2016.01)
*A61B 17/17* (2006.01)
*A61F 2/36* (2006.01)
*G05B 19/418* (2006.01)
*B33Y 80/00* (2015.01)
*A61B 17/56* (2006.01)
*A61F 2/30* (2006.01)
*A61F 2/50* (2006.01)

(52) U.S. Cl.
CPC ............ *A61B 34/10* (2016.02); *A61B 17/175* (2013.01); *A61F 2/3609* (2013.01); *G05B 19/41885* (2013.01); *A61B 2017/568* (2013.01); *A61B 2034/102* (2016.02); *A61B 2034/105* (2016.02); *A61B 2034/107* (2016.02); *A61B 2034/108* (2016.02); *A61F 2/3603* (2013.01); *A61F 2002/30878* (2013.01); *A61F 2002/505* (2013.01); *B33Y 80/00* (2014.12); *Y02P 90/14* (2015.11); *Y02P 90/20* (2015.11)

(58) Field of Classification Search
CPC .............................. A61B 34/10; A61B 17/175
See application file for complete search history.

(56) References Cited

U.S. PATENT DOCUMENTS 5,150,304 A * 9/1992 Berchem ............. A61F 2/30942
623/901
6,033,415 A * 3/2000 Mittelstadt ............ G06T 3/0006
128/922
(Continued)

OTHER PUBLICATIONS

EP Examination Report, EP09718041.8, dated Jul. 27, 2018.

*Primary Examiner* — Christian A Sevilla
(74) *Attorney, Agent, or Firm* — Polsinelli PC

(57) ABSTRACT

Disclosed herein is a surgical guide tool for use in total hip replacement surgery. The surgical guide tool may include a customized mating region and a resection guide. The customized mating region and the resection guide are referenced to each other such that, when the customized mating region matingly engages a surface area of a proximal femur, the resection guide will be aligned to guide a resectioning of the proximal femur along a preoperatively planned resection plane.

20 Claims, 29 Drawing Sheets

Related U.S. Application Data division of application No. 12/391,008, filed on Feb. 23, 2009, now Pat. No. 9,408,618.

(60) Provisional application No. 61/111,238, filed on Nov. 4, 2008, provisional application No. 61/108,761, filed on Oct. 27, 2008, provisional application No. 61/032,671, filed on Feb. 29, 2008.

(56) References Cited

U.S. PATENT DOCUMENTS

| | | |
|---|---|---|
| 6,757,582 B2 | 6/2004 | Brisson et al. |
| 2005/0059978 A1* | 3/2005 | Sherry .................. A61B 17/15 606/87 |
| 2009/0254093 A1* | 10/2009 | White .................. A61B 17/175 606/89 |

* cited by examiner

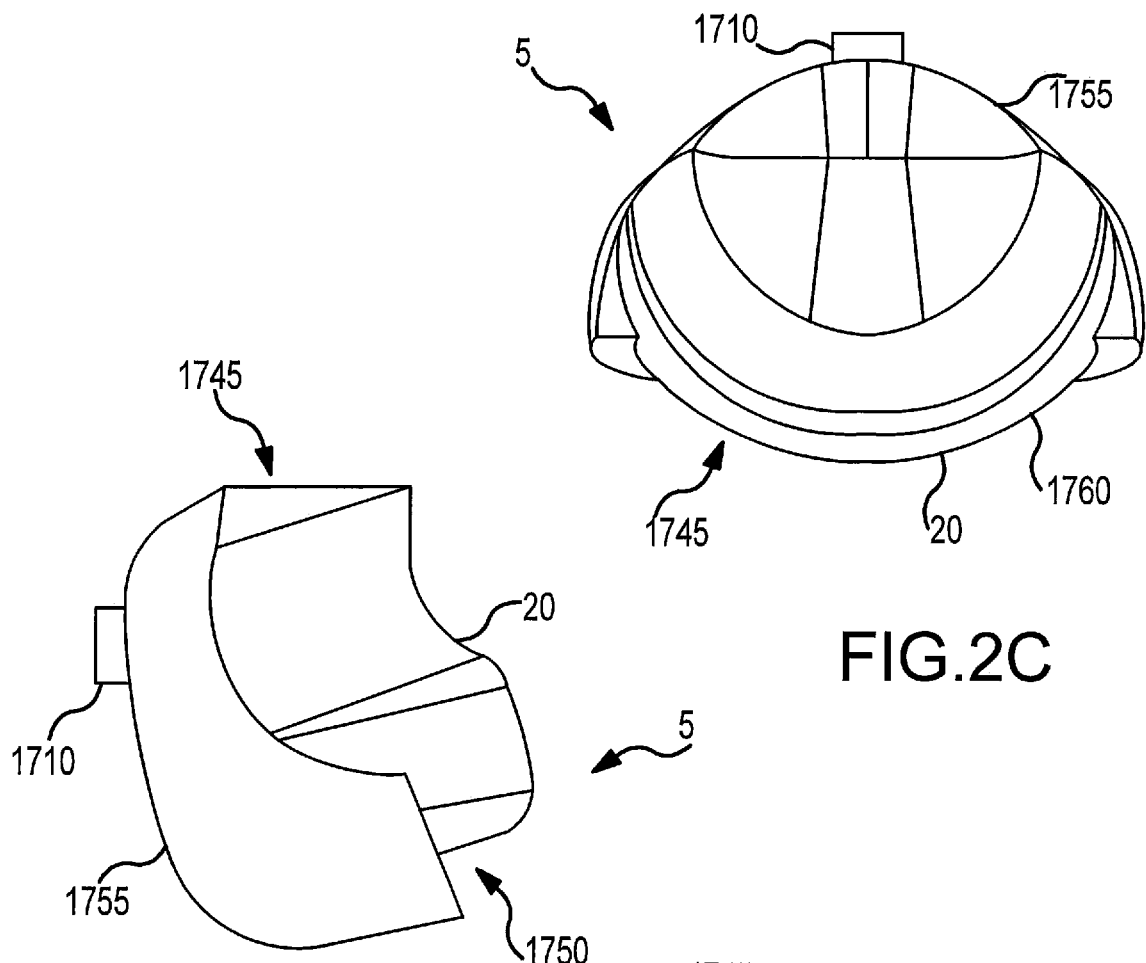
FIG.2C
FIG.2D
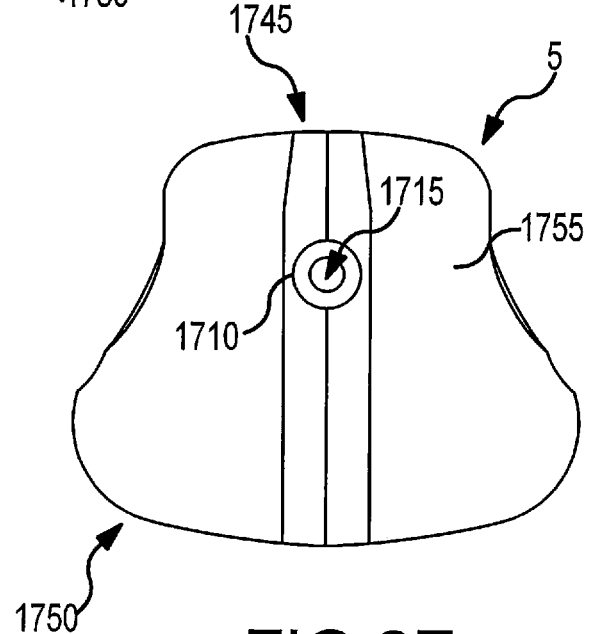
FIG.2E

TOTAL HIP REPLACEMENT SURGICAL GUIDE TOOL

CROSS REFERENCE TO RELATED APPLICATIONS

The present application is a continuation of U.S. application Ser. No. 15/202,417 filed Jul. 5, 2016, which application is a divisional of U.S. application Ser. No. 12/391,008 filed Feb. 23, 2009, now U.S. Pat. No. 9,408,618, which application claims benefit of priority under 35 U.S.C. 119(e) to: U.S. Patent Application Ser. No. 61/032,671, entitled Hip Resurfacing Surgical Guide Tool and filed Feb. 29, 2008; U.S. Patent Application Ser. No. 61/108,761, entitled Hip Resurfacing Surgical Guide Tool and filed Oct. 27, 2008; and U.S. Patent Application Ser. No. 61/111,238, entitled Total Hip Replacement Surgical Guide Tool and filed Nov. 4, 2008. The foregoing applications are hereby incorporated by reference into the present application in their entireties.

The present application also incorporates by reference in its entirety U.S. patent application Ser. No. 12/390,667, filed Feb. 23, 2009, now U.S. Pat. No. 8,734,455 entitled Hip Resurfacing Surgical Guide Tool.

FIELD OF THE INVENTION

The present invention relates to medical apparatus and methods. More specifically, the present invention relates to total hip replacement surgical guide tools and methods of manufacturing and using such tools.

BACKGROUND OF THE INVENTION

Arthroplasty is an orthopedic surgical procedure in which a dysfunctional or arthritic joint surface is replaced, remodeled or redesigned to alleviate pain, restore range of motion or to fix physical joint damage caused by a fracture. Total Hip Replacement ("THR") surgery, also known as hip arthroplasty, is a surgical procedure wherein the proximal femur, with its femoral head and neck, is removed and a prosthetic device (or stem) having a prosthetic femoral head is implanted into the femur. The acetabulum, or hip socket, is also replaced or modified to accept a cup. The cup is configured to receive the prosthetic head. The prosthetic device (or stem) is typically made of titanium or a titanium alloy. The head may be made of a biocompatible plastic, ceramic or other suitable material. The cup may be made of a biocompatible plastic or other suitable material. The prosthetic device and the cup are typically anchored to the bone with bone cement.

Typically, in THR, the surgeon will take a number of measurements by hand or x-ray scan related to proper selection of the prosthetic device, limb length, and hip rotation. During surgery, after making an incision, the femur is pushed out of socket to expose the joint cavity and the deteriorated or damaged femoral head is removed. The femur is then prepared to receive the stem by cleaning and enlarging the hollow center portion of the bone, thereby creating a cavity that matches the shape of the implant stem. The top end of the femur is planed and smoothed so the stem can be inserted flush with the bone surface. If the head is a separate piece, the proper size is selected and attached. Finally, the head is seated within the cup so the joint is properly aligned and the incision is closed.

Hand measuring techniques and x-ray scans are inaccurate and increase the error rate or potential for error in a THR, and may lead to an improperly positioned prosthetic device. Improper positioning of the prosthetic device can result in a change of leg length, dislocation of the hip or perforation of the femur.

There is a need in the art for a total hip replacement surgical guide tool to aid in properly positioning the prosthetic device that reduces the potential for error and improper positioning in a THR. There is also a need in the art for a method of manufacturing such a surgical guide tool.

BRIEF SUMMARY OF THE INVENTION

Disclosed herein is a tool for positioning a prosthetic device in a femur that is the subject of a total hip replacement surgery. In one embodiment, the tool includes an index surface and a saw slot. The index surface is configured to matingly receive a predetermined surface of the femur. The index surface and the saw slot are integrated with each other such that when the index surface matingly receives the predetermined surface of the femur, the saw slot corresponds with the resection plane of the femur.

Disclosed herein is surgical guide tool for use in the preparation of a proximal portion of a femur for the implantation of a total hip replacement prosthetic implant, the implant including a feature configured to abut against a resection surface of the proximal femur when the implant is fully implanted in the proximal femur in a manner that generally replicates a preoperatively planned implantation for the implant. In one embodiment, the tool includes a mating region and a saw guide. When the mating region matingly contacts the proximal portion, the saw guide is aligned with a resection plane generally corresponding to the resection surface. In one version of the embodiment, the saw guide includes at least one planar surface. In one version of the embodiment, the at least one planar surface forms a saw slot.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a superior-posterior region of the neck. The at least a portion of a superior-posterior region of the neck starts between approximately 1 mm and approximately 5 mm after a cartilage covering the head terminates distally and extending between approximately 15 mm and approximately 35 mm towards a trochanteric fossa. In version of the embodiment, the saw guide includes at least one planar surface. In one version of the embodiment, the at least a portion of a superior-posterior region of the neck has an inferior border that begins approximately midway along an intertrochanteric crest and follows along the axis of the neck. In one version of the embodiment, the at least a portion of a superior-posterior region of the neck has a superior border between approximately 1 mm and approximately 3 mm below a junction between superior and anterior surfaces of the neck.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a superior-posterior region of the neck. The at least a portion of a superior-posterior region of the neck includes a narrow band that follows along an intertrochanteric crest and has a medial-lateral width of between approximately 0.5 mm and approximately 8 mm. In one version of the embodiment, the saw guide includes at least one planar surface. In one version of the embodiment, the at least a portion of a superior-posterior region of the neck begins approximately midway along the intertrochanteric crest and extends at least approximately 5 mm towards a most superior tip of a posterior surface of a greater trochanter.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a superior-anterior region of the neck. The at least a portion of a superior-anterior region of the neck starts between approximately 1 mm and approximately 5 mm after a cartilage covering the head terminates distally and extends between approximately 15 mm and approximately 35 mm to terminate before a tubercle. In one version of the embodiment, the saw guide includes at least one planar surface. In one version of the embodiment, the at least a portion of a superior-anterior region of the neck has a superior border approximately 1 mm to approximately 3 mm below a junction between superior and anterior surfaces of the neck. The at least a portion of a superior-anterior region of the neck may have an inferior border that is between approximately 5 mm and approximately 10 mm from the superior boarder. In one version of the embodiment, the at least a portion of a superior-anterior region of the neck lies on an anterior greater trochanter, distal to a tubercle, and inferior to an origin of an obturator internus. The at least a portion of a superior-anterior region may have a medial-lateral distance that measures between approximately 3 mm to approximately 14 mm. The at least a portion of a superior-anterior region may have an inferior-superior distance that measures between approximately 3 mm to approximately 10 mm.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a superior-posterior region of the neck and at least a portion of a superior-anterior region of the neck, but does not include a junction between the superior-posterior and superior-anterior regions of the neck. In one version of the embodiment, the saw guide includes at least one planar surface. In one version of the embodiment, the at least a portion of the superior-posterior region of the neck includes an area that extends along the intertrochanteric chest, but does not include an area that spans portions of a trochanteric fossa. The at least a portion of a superior-anterior region of the neck may lay on an anterior greater trochanter, distal to a tubercle, and inferior to an origin of an obturator internus, but does not include portions of the tubercle.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a posterior region of the neck. The at least a portion of the posterior region of the neck includes an area that extends towards a trochanteric fossa between approximately 15 mm and approximately 35 mm from a first point being between approximately 1 mm and approximately 5 mm distal of a distal termination of a cartilage covering the head. In one version of the embodiment, the saw guide includes at least one planar surface. In one version of the embodiment, the at least a portion of a posterior region of the neck has an inferior border that terminates up to approximately 5 mm superior to a border between posterior and inferior surfaces of the neck. In one version of the embodiment, the at least a portion of a posterior region of the neck has a superior border that terminates approximately 0 mm to approximately 5 mm posterior of a border between posterior and anterior surfaces of the neck. In one version of the embodiment, the at least a portion of a posterior region of the neck extends along an intertrochanteric crest from a lesser trochanter to a point near a tip of a greater trochanter. The at least a portion of a posterior region of the neck does not include at least one of a portion of the trochanteric fossa and a portion of posterior region of the greater trochanter.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a posterior region of the neck. The at least a portion of the posterior region of the neck includes an area that includes a narrow band measuring between approximately 0.5 mm and approximately 12 mm and following along an intertrochanteric crest. In one version of the embodiment, the saw guide includes at least one planar surface. In one version of the embodiment, the narrow band begins approximately 0 mm to approximately 12 mm superior to a lesser trochanter. The narrow band may extend approximately 0 mm to approximately 18 mm inferior to a most superior tip of a posterior surface of a greater trochanter.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a posterior region of the neck. The at least a portion of the posterior region of the neck includes an area that extends towards a trochanteric fossa from a first point being between approximately 1 mm and approximately 5 mm distal of a distal termination of a cartilage covering the head, but does not include an area spanning portions of the trochanteric fossa. In one version of the embodiment, the saw guide includes at least one planar surface. In one version of the embodiment, The tool of claim 32, wherein the area spanning portions of the trochanteric fossa has a width generally transverse to a femoral longitudinal axis of between approximately 0 mm and approximately 20 mm. In one version of the embodiment, the at least a portion of the posterior region of the neck further includes an area that includes a band following along an intertrochanteric crest, but does not include portions of a posterior greater trochanter. In one version of the embodiment, the portion of the posterior greater trochanter has a distally extending dimension of between approximately 0 mm and approximately 12 mm.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of an anterior region of the neck. The at least a portion of an anterior region of the neck extends up to approximately 8 mm laterally past an intertrochanteric line. In one version of the embodiment, the saw guide includes at least one planar surface. In one version of the embodiment, the surface region includes a medial surface of a greater trochanter.

Disclosed herein is a surgical guide tool for use in total hip replacement surgery on a proximal portion of a femur having a head, a neck extending distally from the head, and a surface region distal the head. In one embodiment, the tool includes a body including a saw guide and a mating region configured to matingly contact the surface region. The saw guide and mating region are positioned relative to each other so the saw guide is positioned to guide a resection that generally corresponds to a preoperatively planned resection plane when the mating region matingly contacts the surface region. The surface region includes at least a portion of a lateral posterior greater trochanter. In one version of the embodiment, the saw guide includes at least one planar surface. In one version of the embodiment, the surface region further includes at least a portion of a medial posterior greater trochanter. The surface region may not include at least a portion of an intertrochanteric crest. In one version of the embodiment, the surface region further includes at least a portion of a posterior region of the neck. The surface region does not include at least a portion of a trochanteric fossa. In one version of the embodiment, the surface region further includes at least a portion of a medial posterior greater trochanter and at least a portion of a posterior region of the neck, and wherein the surface region does not include at least a portion of an intertrochanteric crest and does not include at least a portion of an trochanteric fossa.

Disclosed herein is a surgical guide tool for use in total hip replacement surgery on a proximal portion of a femur. In one embodiment, the tool includes a mating region and a saw guide. The mating region matingly contacts the proximal portion. The saw guide is generally aligned with a preoperatively planned resection plane. In one version of the embodiment, the saw guide includes at least one planar surface. The at least one planar surface may form a saw slot. In one version of the embodiment, the mating region includes contact surfaces and non-contact surfaces, wherein, when the mating region matingly contacts the proximal portion, the contact surfaces matingly contact surfaces of the proximal portion opposing the contact surfaces, and the non-contact surfaces are spaced apart from surfaces of the proximal portion opposing the non-contact surfaces. The non-contact surfaces may be a result of an overestimation process.

Disclosed herein is a method of manufacturing a surgical guide tool for use in total hip replacement surgery on a proximal portion of a femur having a head, a neck extending distally from the head, and a surface region distal the head. In one embodiment, the method include: a) generating medical imaging data associated with the proximal portion of the femur; b) employing the imaging data to generate a three-dimensional computer-generated femur model of the proximal portion of the femur; c) providing a three-dimensional computer-generated implant model; d) providing a three-dimensional computer-generated tool model of at least a portion of at least a surgical guide tool and a surgical guide tool blank; e) superimposing the femur model and implant model; f) superimposing the tool model with the superimposed femur model and implant model; g) computer generating manufacturing instructions from data determined from step f; and h) employing the manufacturing instructions at a manufacturing machine to generate the surgical guide tool.

In one version of the embodiment, the surgical guide tool is generated from a surgical guide tool blank. In one version of the embodiment, the implant model includes a shaft portion and a head portion. Superimposing the femur model and implant model may include: causing a center of the head of the implant model to generally coincide with a center of a head of the femur model; and causing the shaft of the implant model to generally align with a shaft of the femur model.

In one version of the embodiment, superimposing the tool model with the superimposed femur model and implant model includes causing the superimposed location of the tool model to generally correspond to a tool position to be employed by a selected surgical approach. In one version of the embodiment, the method further includes providing at least one of a three-dimensional computer generated sphere model and a computer generated rod model and at least one of: superimposing the sphere model with the femur model so a center of the sphere model is caused to generally coincide with a center of a head of the femur model; and superimposing the rod model with the femur model so the rod model is caused to generally align with a shaft of the femur model. Superimposing the femur model and implant model may include at least one of: causing a center of the head of the implant model to generally coincide with the center of the sphere model; and causing the shaft of the implant model to generally align with the rod model.

In one version of the embodiment, the medical imaging data is generated via at least one of MRI and CT. In one version of the embodiment, the manufacturing machine is at least one of a CNC machine and a SLA.

In one version of the embodiment, the method further includes subjecting the medical imaging data to a segmentation process that determines bone contour lines and then adjusting the bone contour lines outward in locations of the bone contour lines corresponding to regions of the proximal portion of the femur that have surface topography that is unlikely to be accurately replicated during at least one of a three-dimensional computer modeling process and generating the tool via the machine. The surface topography may be at least one of highly varied and too small to be manufactured into the tool. The method may further include employing the adjusted bone contour lines to generate the three-dimensional computer-generated femur model of the proximal portion of the femur. The regions of the proximal portion of the femur that have surface topography that is unlikely to be accurately replicated may include at least one of a portion of a tubercle and a portion of a superior intersection between anterior and posterior regions of the neck. The regions of the proximal portion of the femur that have surface topography that is unlikely to be accurately replicated may include at least one of a portion of a trochanteric fossa and a portion of a superior intersection between anterior and posterior regions of the neck. The regions of the proximal portion of the femur that have surface topography that is unlikely to be accurately replicated may include at least one of a portion of a trochanteric fossa and a portion of a posterior greater trochanter near an intertrochanteric crest. The regions of the proximal portion of the femur that have surface topography that is unlikely to be accurately replicated may include at least one of a portion of a trochanteric fossa and a portion of an intertrochanteric crest.

In one version of the embodiment, the data determined from step f includes a resection plane corresponding to a planar surface of a spacer region of the implant model. The data determined from step f may further include a mating surface corresponding to a region of the femur model contacted by the tool model. The mating surface and resection plane may be positionally referenced to each other. The mating surface and resection plane may be respectively used to define an indexing surface and a saw guide in the tool, the indexing surface and saw guide being configured such that, when the indexing surface matingly contacts the proximal femur, the saw guide will be positioned to facilitate a resection of the proximal femur corresponding to a preoperatively planned resection.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 2C is a front view of the surgical guide tool of FIG. 2B.

FIG. 2D is a side view of the surgical guide tool of FIG. 2B.

FIG. 2E is a top plan view of the surgical guide tool of FIG. 2B.

DETAILED DESCRIPTION

Figure 1A:
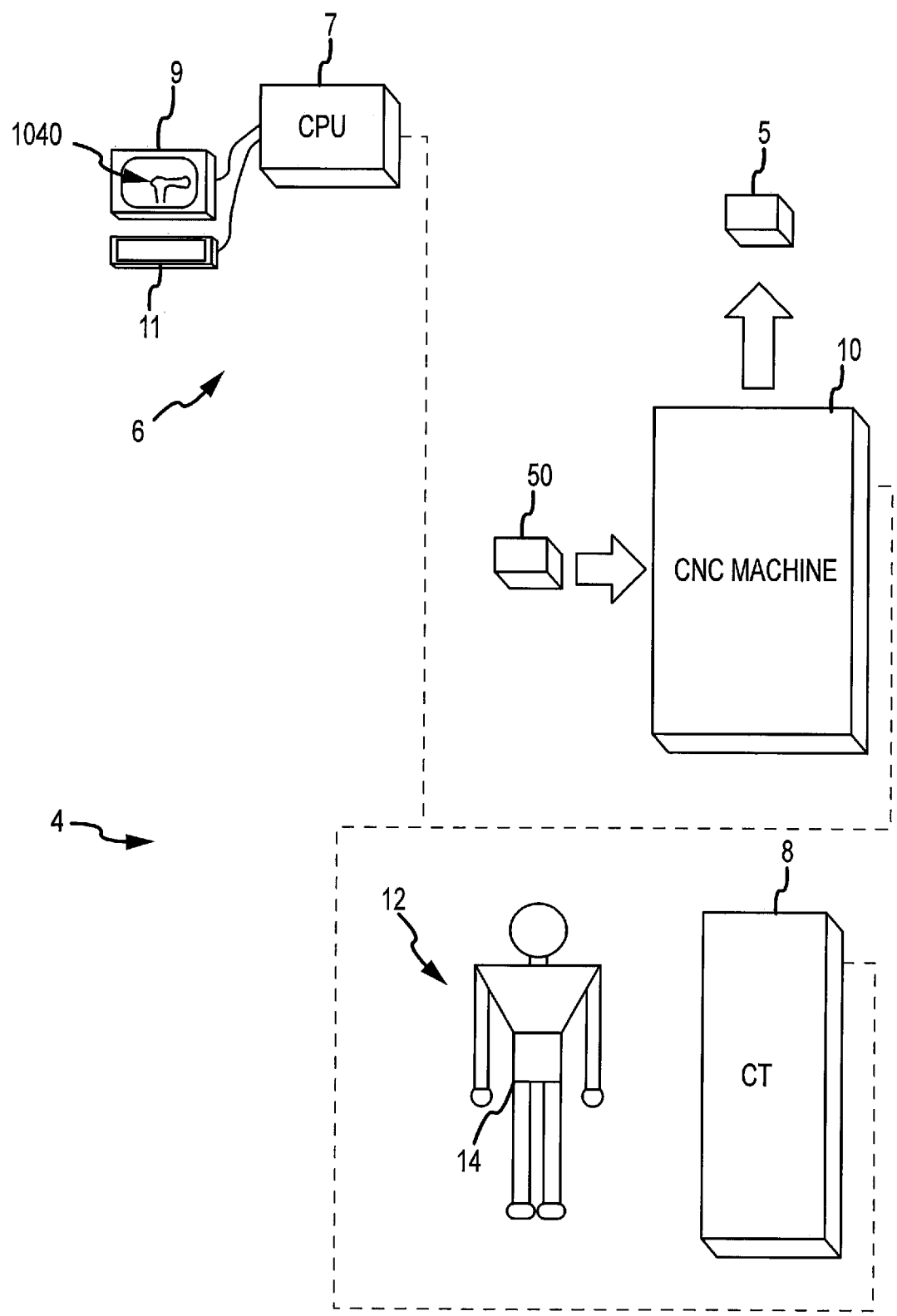
FIG. 1A is a diagrammatic depiction of a system for preoperatively planning and manufacturing a surgical guide tool as described herein.

I. Overview of Tool and its Methods of Planning, Manufacturing and Use

The present disclosure describes a customized surgical guide tool 5 for use in total hip replacement surgery ("THR"). In one embodiment, the customized surgical guide tool 5 may be preoperatively planned via three-dimensional ("3D") computer modeling procedures such that, when the tool 5 is matingly engaged with the proximal femur 40 of the patient, a resection guided by the tool 5 will result in a desired resection that will allow a femoral prosthetic implant or component 800 to be implanted in the femur 40 as planned during the preoperative planning.

In one embodiment, the tool 5 may include a single-piece construction, a fastener receiving feature 1710, a customized saw guide 1725, and a customized indexing or mating region 20 having customized indexing or mating surfaces 708a, 710a. The fastener receiving feature 1710 may be used to receive an anchor that may secure the tool 5 in mating engagement with the proximal femur 40.

The mating region 20 and its mating surfaces 708a, 710a may be configured such that, when the mating region 20 matingly receives therein a region of the proximal femur 40 having predetermined bone surfaces 708, 710, the mating surfaces 708a, 710a of the mating region 20 of the tool 5 will matingly contact the predetermined bone surfaces 708, 710 on the proximal femur 40. The mating region 20 may also include non-contacting surfaces 718a, 720a that correspond to surfaces of proximal femur 40 that are within the region of the femur engaged by the tool mating region 20 and that have surface topography of such variation that it is difficult to accurately scan or computer model or too small to manufacture into the tool mating region. These non-contacting surfaces 718a, 720a of the tool mating region 20 may be the result of an overestimation process during image segmentation and will be spaced apart in a non-contacting fashion from the adjacent femur surfaces when the tool mating region 20 matingly receives the femur 40.

The saw guide 1725 may be a slot, planar surface, or other feature capable of guiding a saw blade during a sawing procedure. The saw guide 1725 may be positioned and oriented relative to the customized mating or indexing region 20 such that, when the mating surfaces 708a, 710a of the mating region 20 matingly contact the bone surfaces 708, 710 when the tool mating region 20 matingly receives therein the region of the femur 40 having the bone surfaces 708, 710, the saw guide 1725 may be oriented over the femur neck 35 such that the saw guide 1725 corresponds with a desired resection plane 805 through the femoral neck 35 that was identified during the preoperative planning. The resection plane 805 may correspond with a spacer region 801 of the femoral prosthetic implant or component 800 that limits the extent to which the femoral component may be inserted into the resected proximal femur during implantation.

When the mating or indexing surfaces 708a, 710a of the mating region 20 of the tool 5 matingly contact the bone surfaces 708, 710 as the mating region 20 mating receives the region of the femur including the bone surfaces 708, 710, a saw extending through the saw slot 1725 will be caused to saw through the femur neck 35 at the desired and preoperatively planned resection plane 805, thereby creating a resected portion of the neck 35 that is configured to receive an implanted femoral component 800 in a manner that replicates the preoperatively planned implant position and alignment. Once the femur resection is completed with the tool 5 and the femur is further prepped as needed, the femoral component 800, which may be selected based on the information obtained during the preoperative planning, may then be inserted into the resected proximal femur 40.

As stated above, in some embodiments, the tool 5 may have a single-piece construction, which may increase the accuracy associated with the resectioning process by minimizing tolerance errors normally associated with multi-piece, multi-joint, conventional guide tools. In other embodiments, the tool 5 may have a multi-piece construction. For example, the saw slot 1725 may be in the form of a separate guide that is mounted on the rest of the tool 5 in an indexed manner, the rest of the tool 5 having the customized mating region having the customized mating surfaces.

The guide tool 5 aids the surgeon in accurately implanting the femoral component 800 during a THR according to an alignment and position determined during preoperative planning. Specifically, the tool 5, once matingly engaged with the proximal femur, may guide the resection of the proximal femur according to a resection plane identified during the preoperative planning. Accurate implant alignment and position is important because an improperly positioned and aligned femoral component 800 may result in a change of leg length, dislocation of the hip or perforation of the femur.

Furthermore, because the tool 5 is configured to generally automatically provide an appropriate resection through the femur neck for a proper alignment of the femoral component upon causing the indexing region 20 to matingly receive the region of the femur having the bone surfaces 708, 710, the time and effort required by the surgeon to properly prepare the femur for the implantation of the femoral component 800 is substantially minimized. Thus, use of the tool 5 may reduce the overall time spent in surgery. The reduction in the time spent in surgery may reduce the patient's chances of infection.

In some embodiments, a three dimensional ("3D") model of the patient's proximal femur 40 is computer generated from two dimensional ("2D") medical imaging slices 500 (e.g., CT slices, MRI slices, etc.) taken of the patient's proximal femur 40. A sphere 3D computer model 701 and a rod 3D computer model 702 may be respectively aligned with the femoral head 30 and medullary canal 170 or the central axis 100 of the femur shaft of the femur 3D computer model 1040 to approximate the positioning of the femoral component 800 relative to the center of the hip joint 703. A 3D model of the femoral component 800 may be selected from a database of 3D models of candidate femoral component 800. The selected 3D model of the femoral component may be aligned with the 3D model of the femur 40 and the sphere and rod models 701, 702 such that the component head is generally centered with the center of the sphere model and the component shaft is generally coaxial with the rod model.

A 3D model of a blank of the tool 5 may be positioned on the femur model, which is still aligned with the sphere, rod and femoral component models 701, 702, 800. The resection plane may be determined from the location of a spacer region surface or distal end 803 of a spacer region 801 of the femoral component 800 and used to define a saw slot 1725 in the 3D model of the blank of the tool 5. The 3D model of the femur is analyzed to determine shape and location of the mating or indexing femur surfaces 708, 710. The shape and location of the surfaces 708, 710 may be used to define corresponding mating surfaces 708a, 710a in the mating region 20 of the 3D model of the blank of the tool 5. The indexing surfaces 708a, 710a of the mating region 20, the saw slot 1725, and the orientation relationships between the surfaces 708a, 710a and the saw slot 1725 may be imported into the 3D computer generated model of the blank of the tool 5. As the 3D femur model, 3D sphere model, 3D rod model and 3D tool blank model are superimposed relative to each other in the above-described orientation and positioning, the surfaces 708a, 710a and saw slot 1725 end up being defined and imported into the 3D tool blank model such that a resulting tool 5 will position the saw slot 1725 to create the preoperatively planned resection in the femur when the mating surfaces 708a, 710a of the mating region 20 matingly contact the femur surfaces 708, 710 when the mating region 20 matingly receives the region of the femur having the femur surfaces 708, 710. The resulting 3D model of the blank of the tool 5 may be used to generate manufacturing instructions (e.g., machining paths, etc.), which are sent to an automated manufacturing device, such as a CNC machine, a stereolithography apparatus ("SLA"), etc. to mill or otherwise manufacture an actual tool 5 from an actual tool blank 50.

As can be understood from the preceding discussion and as discussed in greater detail below, by superimposing a 3D computer generated model of the patient's proximal femur 40 with the 3D computer generated models of the femoral component 800, sphere, and rod, the proper placement and alignment of the femoral component 800 through the proximal femur 40 can be preoperatively planned with a great degree of accuracy. Also, by superimposing the 3D computer generated model of the blank of the tool 5 with the superimposed 3D computer generated models of the patient's femur 40 and the femoral component 800, the relationships between these models can be analyzed to determine the location and orientation of the saw guide 1725, the location and shape of the indexing surfaces 708a, 710a of the mating region 20, and the positional relationship between the saw guide 1725 and indexing surfaces 708a, 710a, all of which can be imported into the 3D computer generated model of the blank of the tool 5 to define such features into the 3D model of the tool blank.

The resulting 3D computer generated model of the blank of the tool 5 may then be used as manufacturing instructions for the automated manufacture of a customized guide tool 5 having a saw guide 1725 that will result in the preoperatively planned resection of the proximal femur 40 when the tool 5 is matingly engaged with the proximal femur such that the indexing surfaces 708a, 710a mating contact the predetermined femur surfaces 708, 710 when the tool mating region matingly receives the proximal femur 40. Thus, the resulting tool 5 is customized for the specific patient via a preoperative planning process that employs a 3D model of the patient's femur compiled from 2D medical images 500 taken of the patient's femur. The resulting tool 5 includes the "data" physically integrated therein that allows the tool 5 to matingly engage the patient femur 40 and direct the resection of the femur as calculated during the preoperative planning process to facilitate a desired preoperatively planned position and orientation of the implanted femur component 800.

II. Total Hip Replacement Surgical Guide Tool

Figure 2A:
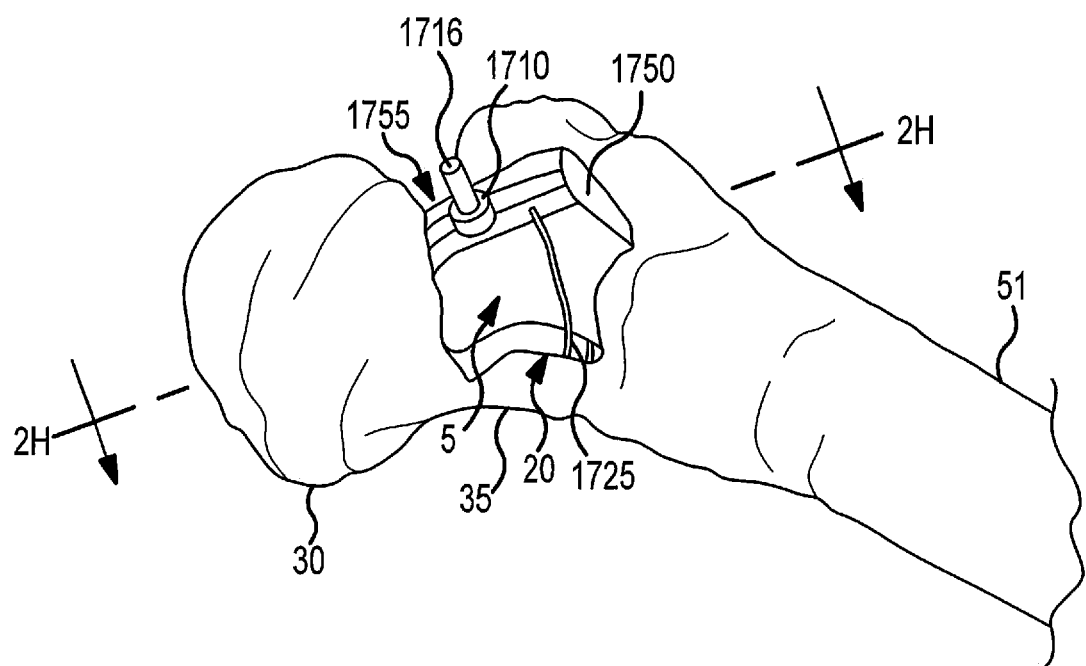
FIG. 2A is an isometric view of a surgical guide tool matingly engaged with a proximal femur having a femoral head and neck.
Figure 2B:
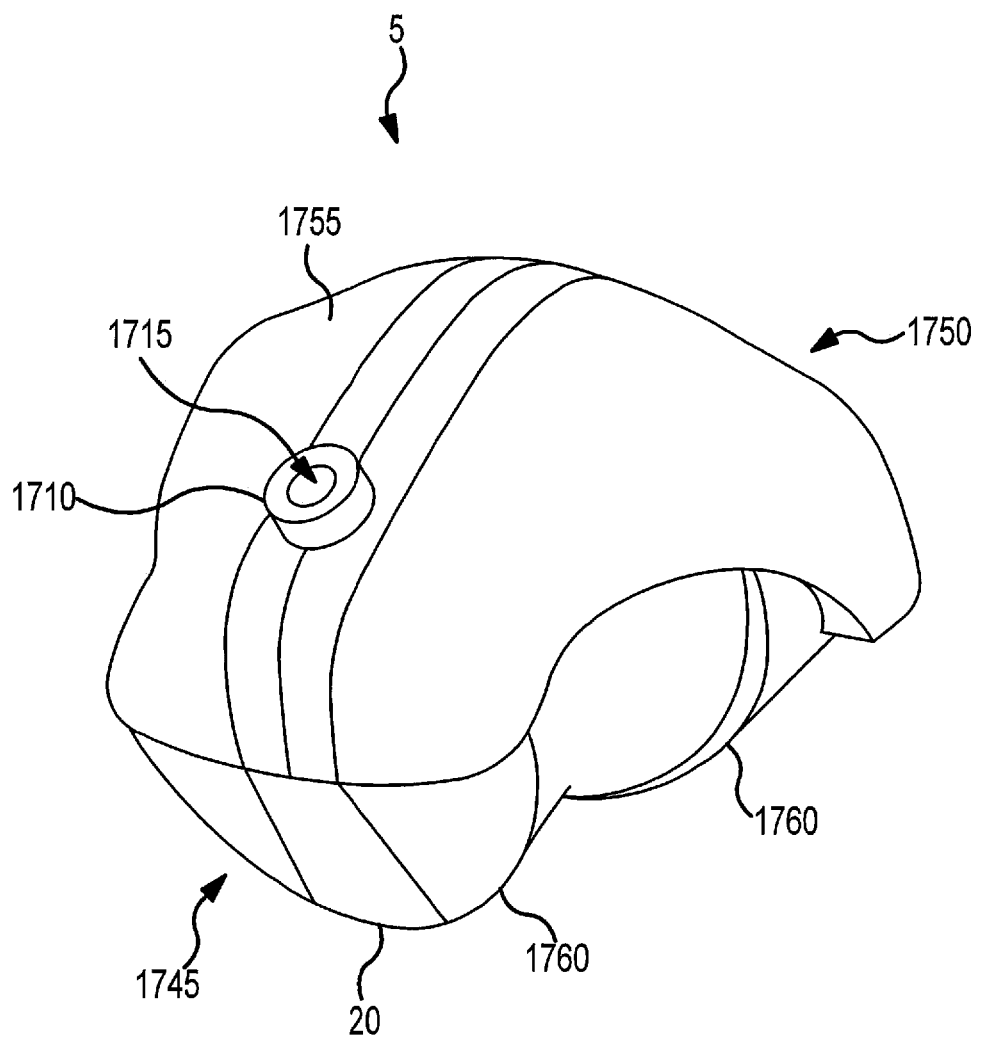
FIG. 2B is a side top isometric view of the surgical guide tool of FIG. 2A, wherein the tool is in a non-customized state or is in the form of a blank from which a customized tool is generated via an automated manufacturing machine, such as, for example, a CNC milling machine.
Figure 2F:
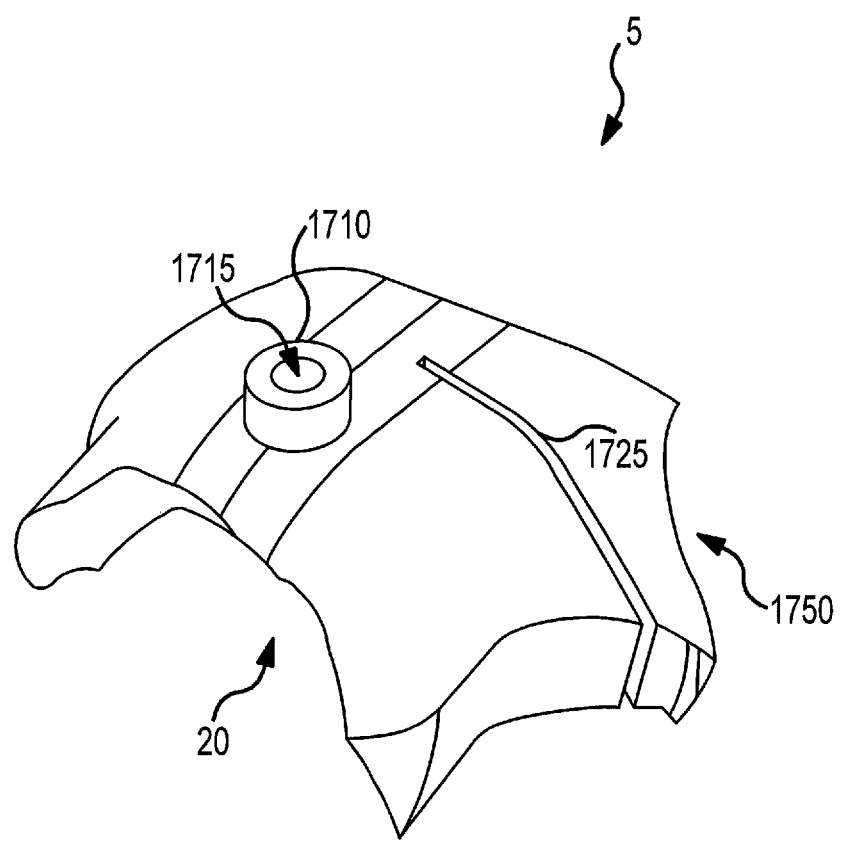
FIG. 2F is the same view as FIG. 2B, except the tool is in the customized state depicted in FIG. 2A and a saw slot is shown.
Figure 2G:
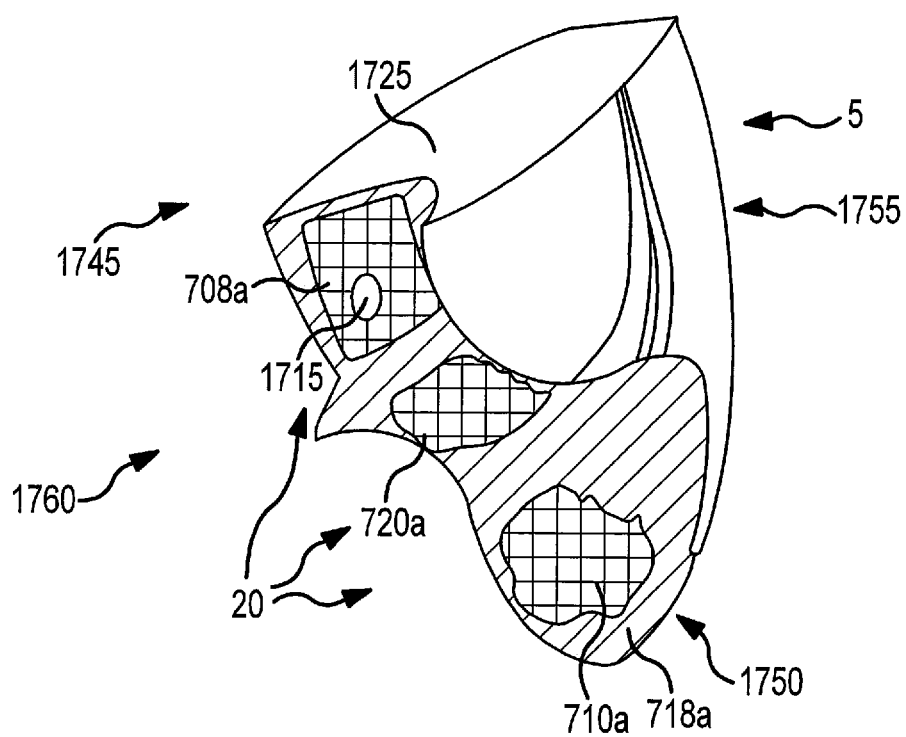
FIG. 2G is a side bottom isometric view of a version of the tool depicted in FIG. 2F, except the tool of FIG. 2G employs a planar surface as the saw guide in place of the saw slot depicted in FIG. 2F, the mating region of the tool of FIG. 2G being configured to engage the mating region of the femur depicted in FIG. 13.
Figure 2H:
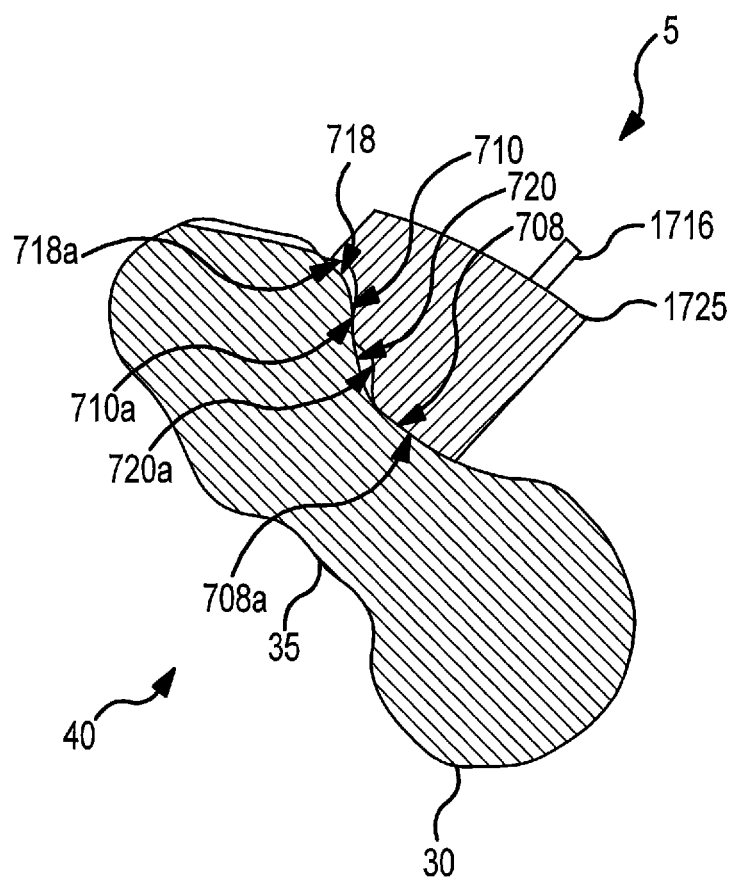
FIG. 2H is a cross section taken through section line 2H-2H, which extends generally posterior-anterior in FIG. 2A, except employing the version of the tool depicted in FIG. 2G.

For a detailed discussion of an embodiment of the surgical guide tool 5 for use in a total hip replacement surgery, reference is made to FIGS. 2A-2H. FIG. 2A is an isometric view of a surgical guide tool 5 matingly engaged on a proximal femur 40 having a femoral head 30 and neck 35. FIG. 2B is a side top isometric view of the surgical guide tool 5 of FIG. 2A, wherein the tool 5 is in a non-customized state or is in the form of a blank from which a customized tool 5 is generated via an automated manufacturing machine, such as, for example, a CNC milling machine. FIGS. 2C-2E are front, side and top plan views, respectively, of the tool 5 of FIG. 2B. FIG. 2F is the same view as FIG. 2B, except the tool 5 is in the customized state depicted in FIG. 2A and a saw slot 1725 is shown. FIG. 2G is a side bottom isometric view of a version of the tool 5 depicted in FIG. 2F, except the tool 5 of FIG. 2G employs a planar surface 1725 as the saw guide 1725 in place of the saw slot 1725 depicted in FIG. 2F, the mating region 20 of the tool 5 of FIG. 2G being configured to engage the mating region of the femur 40 depicted in FIG. 13. FIG. 2H is a cross section taken through section line 2H-2H, which extends generally posterior-anterior in FIG. 2A, except employing the version of the tool 5 depicted in FIG. 2G.

As illustrated in FIGS. 2A-2H, in one embodiment, the surgical guide tool 5 includes a proximal or head end 1745, a distal or greater trochanter end 1750, a top side 1755 and a bottom side 1760. As can be understood from FIGS. 2B-2E, in a non-customized state, the bottom side 1760 and the top side 1755 are generally arcuately shaped. As shown in FIG. 2E, in one embodiment, the width of the tool 5 may gradually increase from the proximal end 1745 to the distal end 1750. The ends 1745, 1750 are formed or otherwise joined together via the bottom side 1760 and top side 1755 such that the tool 5 may be a single-piece tool having a single-piece construction that is generally unitary and continuous in nature. In other embodiments, the tool 5 may have a multi-piece construction, for example, where the saw guide is mounted as a separate and independent piece on the rest of the tool that includes the mating region. The tool 5 may be made of polyoxymethylene (acetal resin), a low density polyethylene, or other biocompatible plastics.

As can be understood from FIGS. 2F-2H, portions of the bottom side 1760 and the top side 1755 may include a customizable mating or indexing region 20 that may have mating contact surfaces 708a, 710a and non-contacting surfaces 718a, 720a defined therein. The mating or indexing region 20 may be adapted to matingly receive regions of the proximal femur 40 having mating contact surfaces 708, 710 and non-contacting surfaces 718, 720 such as those discussed in detail later this Detailed Description with respect to FIG. 13 or similar to those discussed in detail with respect to FIGS. 14A-16B.

For example, as can be understood from FIGS. 2A, 2G, 2H and 13, the region of the femur 40, which may be matingly received by the tool mating region 20 when the tool 5 is mounted on the femur 40, may include a mating contact surface 708 covering portions of the posterior region of the neck 35 and a mating contact surface 710 that is a narrow band following along the intertrochanteric crest 116. Since the tool 5 is customized to fit the patient's specific bone geometry, the mating contact surfaces 708a, 710a of the tool mating region 20 may be configured to matingly contact the mating contact surfaces 708, 710 of the femur 40 when the tool mating region 20 matingly receives therein the region of the femur that has the mating contact surfaces 708, 710. The femur surfaces 708, 710 to be mated or indexed by the tool mating or index surfaces 708a, 710a may be separated by non-contacting surfaces 718, 720 of the femur 40. The non-contacting surfaces 718, 720 of the femur 40 may be spanned in a spaced-apart, non-contacting arrangement by non-contacting surfaces 718a, 720a of the tool mating region 20 when the tool mating region 20 matingly receives the region of the femur 40 including the non-contacting surfaces 718, 720 and the tool mating surfaces 708a, 710a matingly contact the femur contacting surfaces 708, 710. The non-contacting surfaces 718a, 720a of the tool mating region 20 may be the result of an over-estimating process occurring during image segmentation as described later in this Detailed Description. As can be understood from FIG. 13, the non-mating surfaces 718, 720 of the proximal femur 40 may include portions 718 of the posterior greater trochanter 115 and portions 720 of the trochanteric fossa 210 (i.e., the depression between the greater trochanter and the femur neck).

As shown in FIGS. 2B-2E, the top side 1755 may include a fastener-receiving feature 1710. The fastener-receiving feature 1710 may be generally ring shaped and may include a hole 1715 extending axially therethrough. In one embodiment, the top side 1755 includes one fastener-receiving feature 1710. In some embodiments, the top side 1755 includes more than one fastener-receiving feature 1710. The fastener receiving feature 1710 is configured to receive a fastener 1716 through the hole 1715, thereby securing the tool 5 to the femur 40 when the indexing surfaces 708a, 710a of the tool mating region 20 matingly contact the corresponding bone surfaces 708, 710. In some embodiments, the top face does not include a fastener receiving feature 1710 and the tool is secured by other methods, such as being held in place by the surgeon. The fastener 1716 may be a pin, screw or other suitable device.

As can be understood from FIGS. 2F and 2G, in a customized state, the top side 1755 may also include a saw guide 1725 that is configured to receive a saw blade during a THR. The saw guide 1725 may be in the form of a planar surface, a slot or any other feature capable of guiding a saw during a resection. In one embodiment, the saw slot 1725 is generally an open-ended rectangle and extends axially through the tool 5 from the top side 1755 to the bottom side 1760. In some embodiments, the saw slot 1725 may extend across the entire width of the neck 35 such that the surgeon may make a complete resection of the neck. In some embodiments, the saw slot 1725 may extend at least partially across the width of the neck such that the surgeon may make a partial neck resection.

As will be discussed in more detail below with respect to FIG. 12, the saw slot 1725 may be positioned in the tool 5 such that the slot 1725 is aligned with a preoperatively planned resection plane 805, as determined by 3D modeling. The resection plane 805 may correspond with a spacer region 801 of the femoral prosthetic implant or component 800 that limits the extent to which the femoral component may be inserted into the resected proximal femur during implantation. The resection plane 805 defines the location of the head and neck resection during surgery. Thus, when a saw blade is inserted into the saw slot 1725, the subsequent cut through the neck 35 of the proximal femur 40 will expose a portion of the neck 35 for receipt of the femoral component 800. Because the location of the saw slot 1725 is determined based on preoperative planning employing 3D models of the patient's femur and the specific implant 800 to employed in the THR, the subsequent cut through the neck is positioned to expose a portion of the neck aligned to receive the femoral component 800 such that the femoral component 800 may be accurately positioned upon insertion into the femur.

III. System for Planning and Manufacture of Tool

The above-described customized guide tool 5 may be designed and manufactured employing a system 4 similar to that schematically depicted in FIG. 1A. As shown in FIG. 1A, the system 4 may include a preoperative planning system 6 in the form of a computer 6 having a CPU 7, a monitor or screen 9 and operator interface controls 11, such as a keyboard, mouse, etc. The computer 6 may be linked to a medical imaging system 8, such as a CT or MRI machine 8, and an automated or rapid manufacturing machine 10, such as a stereolithography apparatus ("SLA") or a computer numerical controlled ("CNC") milling machine 10. The imaging machine 8, the manufacturing machine 10, and the modeling system 6 of the system 4 may be in communication with each other via, for example, hardwire, internet, wireless, portable memory devices or any combination thereof.

The medical imaging machine 8 may be employed to generate medical images 500 of the joint 14 of the patient 12 that is the subject of the arthroplasty. While this Detailed Description is given in the context of the joint 14 being a hip joint 14 and the tool 5 being configured for the preparation of the proximal femur 40 to receive a total hip replacement prosthetic implant, the concepts disclosed herein may be readily applicable to arthroplasty for other types of joints, including, for example, ankles, knees, wrists, elbows, shoulders, vertebra, fingers, toes, etc. Any resulting 2D medical images 500 may be sent to the computer 6 for use in the preoperative planning.

During preoperative planning, an operator may view the various 3D computer generated models, such as the femur model 1040 and others, via the monitor 11 as the operator interacts with the computer 6 via the controls 11 to direct the preoperative planning. Computer programs for creating, storing and manipulating the various 3D computer generated models may be stored in computer memory accessible by the CPU 7. Computer programs for creating the 3D computer generated bone model 1040 from the 2D images 500 include: Analyze from AnalyzeDirect, Inc., Overland Park, Kans.; Insight Toolkit, an open-source software available from the National Library of Medicine Insight Segmentation and Registration Toolkit ("ITK"), www.itk.org; 3D Slicer, an open-source software available from www.slicer.org; Mimics from Materialise, Ann Arbor, Mich.; and Paraview available at www.paraview.org.

Once the preoperative planning is completed, the resulting information is used to create manufacturing instructions that are sent to the automated manufacturing machine 10 to generate the final tool 5, which in some embodiments, may be manufactured from a tool blank 50 placed in the manufacturing machine 10.

IV. Medical Imaging, Image Segmentation and Generation of 3D Bone Model

Figure 1B:
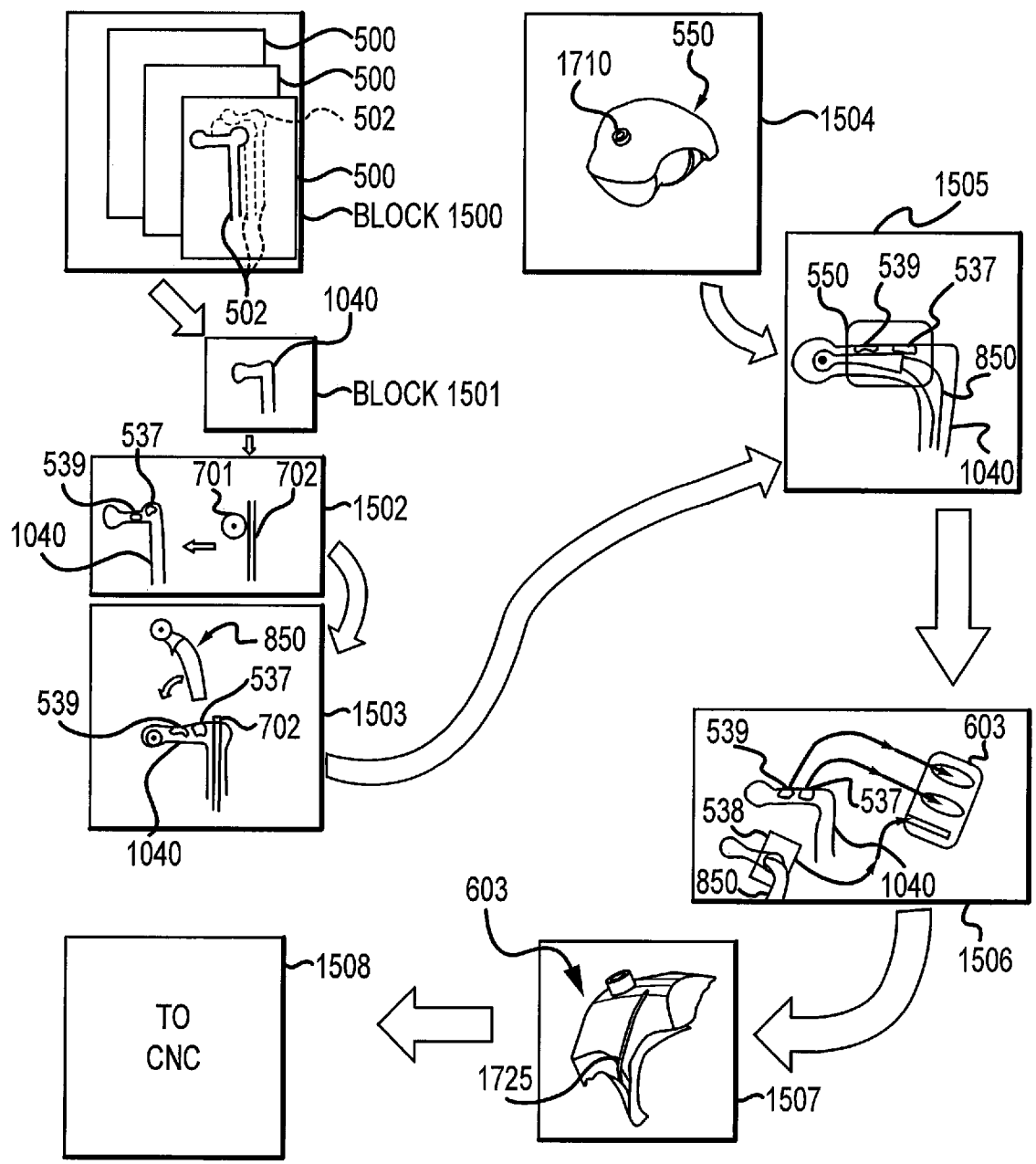
FIG. 1B is a diagrammatic depiction of the preoperative planning process, beginning with the generation of the 2D medical images and ending with the manufacturing instructions being sent to the CNC machine.
Figure 1C:
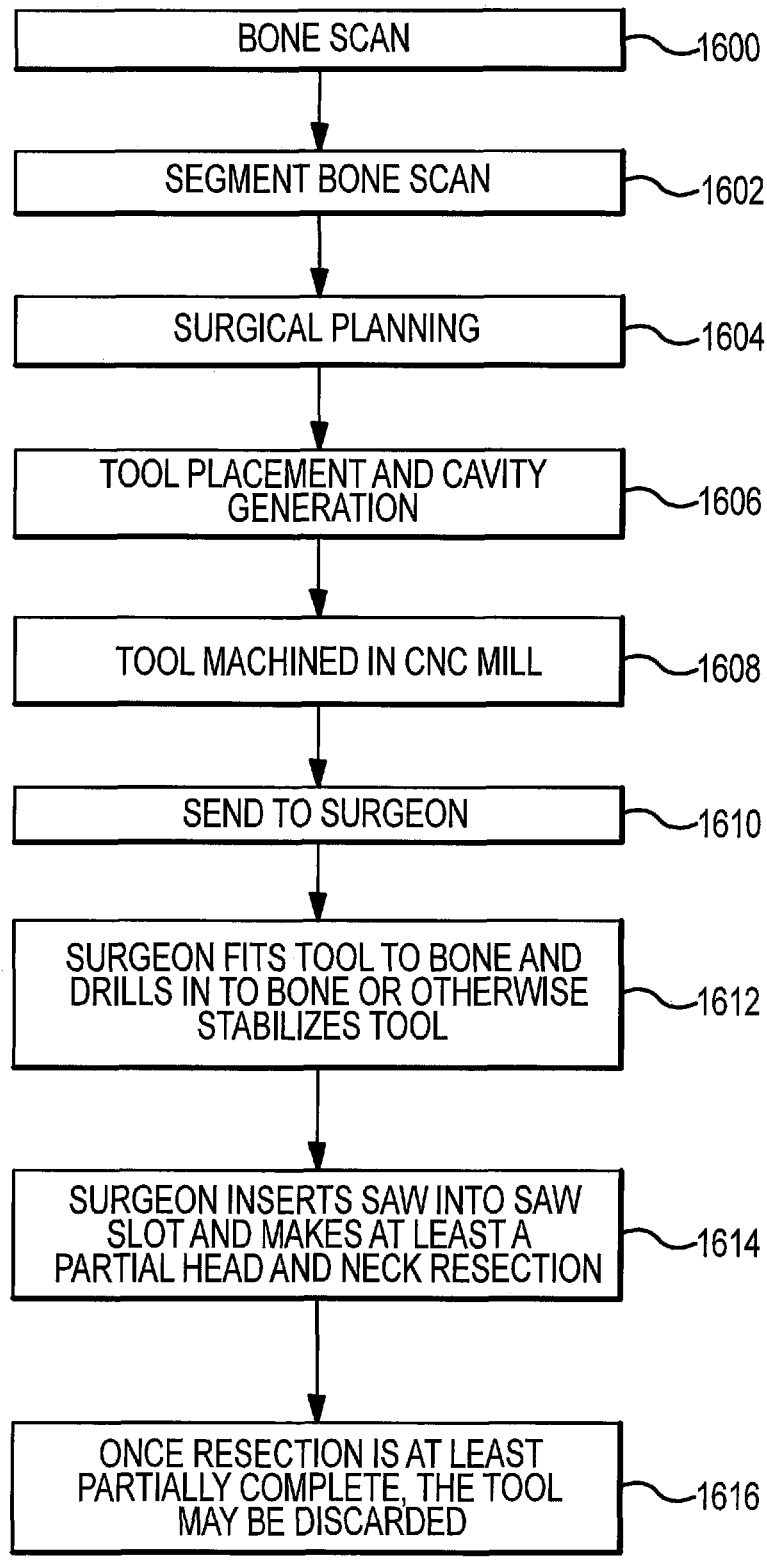
FIG. 1C is a flow chart extending from the generation of the 2D medical images, through the preoperative planning and manufacturing of the tool, and finishing with the tool being employed in the arthroplasty procedure.

For a detailed discussion regarding the medical imaging and image segmentation processes, reference is now made to FIGS. 1A-1C. FIG. 1B is a diagrammatic depiction of the tool planning process, beginning with the generation of the 2D medical images 500 and ending with the manufacturing instructions being sent to the CNC machine 10. FIG. 1C is a flow chart extending from the generation of the 2D medical images 500, through the planning and manufacturing of the tool 5, and finishing with the tool 5 being employed in the arthroplasty procedure.

As indicated in FIGS. 1A-1C, a patient 12 has a hip joint 14 that is the subject of a THR surgery. The hip joint 14 of the patient 12 is scanned in the imaging machine 8 [block 1500 and block 1600]. In one embodiment, the scanning may include up to one-third of the proximal femur 40, including the femoral head 30 and the lesser trochanter 740. In other embodiments, the scanning may include a greater or lesser portion of the femur.

The resolution of a CT scan or an MRI scan is greater than the resolution of x-ray. Greater resolution leads to more accuracy in the preoperative planning process, which leads to greater precision in the resulting tool 5. In some embodiments, the resolution of the scan is between approximately 0 mm and approximately 2 mm. In other embodiments, the resolution of the scan is between approximately 0.3 mm and approximately 0.6 mm. In one embodiment, a CT scan with a resolution of approximately 0.6 mm is utilized for creation of the tool. In one embodiment, a CT scan with a resolution of approximately 0.5 mm to 2 mm, with a tube current ranging from 200 mA to 400 mA and a tube voltage ranging from 120 kV to 140 kV and a direct field of view ("DFOV") ranging from approximately 16 cm to approximately 26 cm is utilized for creation of the tool.

As indicated in FIGS. 1A-1C, in performing the scanning process, the imaging machine 8 makes a plurality of scans of the joint 14, wherein each scan pertains to a thin 2D image slice 500 of the joint 14. The plurality of 2D images 500, which may be CT, MRI or other 2D medical images, are sent from the imaging machine 8 to the preoperative planning system 6. The 2D images are subjected to an image segmentation process, wherein the bone contour lines 502 are identified in each of the images 500 [block 1500 and block 1602].

In one embodiment, the bone surface contour lines of the femur 40 depicted in the image slices 500 may be auto segmented via a image segmentation process as disclosed in U.S. Patent Application Ser. No. 61/126,102, which was filed Apr. 30, 2008, is entitled System and Method for Image Segmentation in Generating Computer Models of a Joint to Undergo Arthroplasty, and is hereby incorporated by reference into the present application in its entirety.

Figure 3:
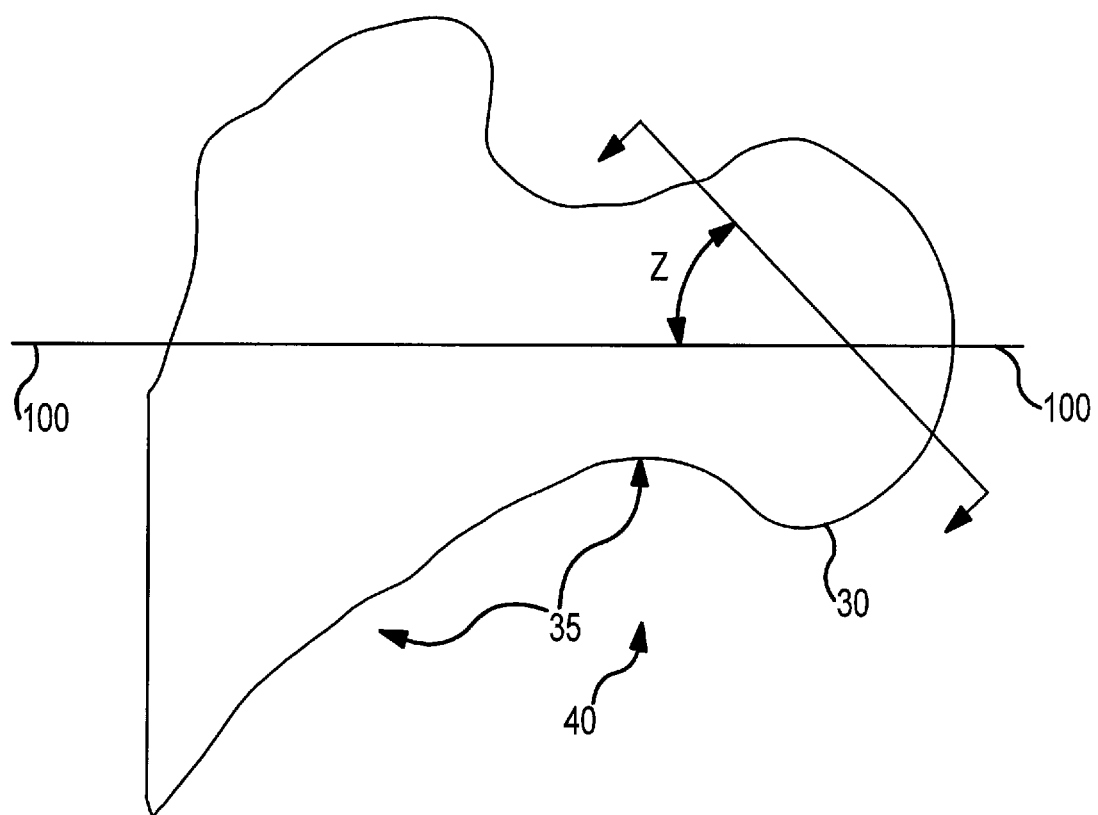
FIG. 3 is a posterior view of a 3D computer generated model of the proximal femur, including its femoral head, neck and greater trochanter, illustrating the angle Z at which the bone scan is sectioned.

As can be understood from FIG. 3, which is a posterior view of a 3D computer generated model of the proximal femur 40, including its femoral head 30, neck 35 and greater trochanter 115, the bone scan may be sectioned for the segmentation process at an angle Z. In other words, in one embodiment, image segmentation is performed utilizing image slices or sections 500 at an angle Z off the central axis 100 of the femoral neck 35 viewed posteriorly. The segmentation can be done in several ways and for ease of the reader are described in relation to a CT-scan. For example, the during the CT scanning of the femur, the CT locator could be positioned at an angle Z to section the CT scan. Alternatively or additionally, the CT scan could be sectioned at an angle Z during post-processing. In one embodiment, the angle Z is between approximately thirty degrees and approximately sixty degrees. In an alternative embodiment, the angle Z is approximately a 45 degree angle. It can be appreciated that segmentation of an MRI scan may be achieved in a similar manner.

Figure 4A:
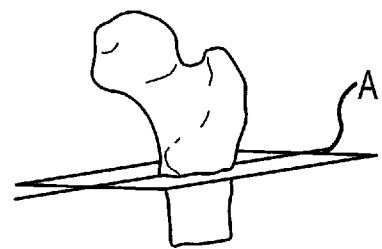
FIG. 4A is a 3D view of the proximal femur of FIG. 2A, illustrating a section line A at which the bone is sectioned during a CT scan to help create a cortical bone model and trabecular bone model.
Figure 4B:
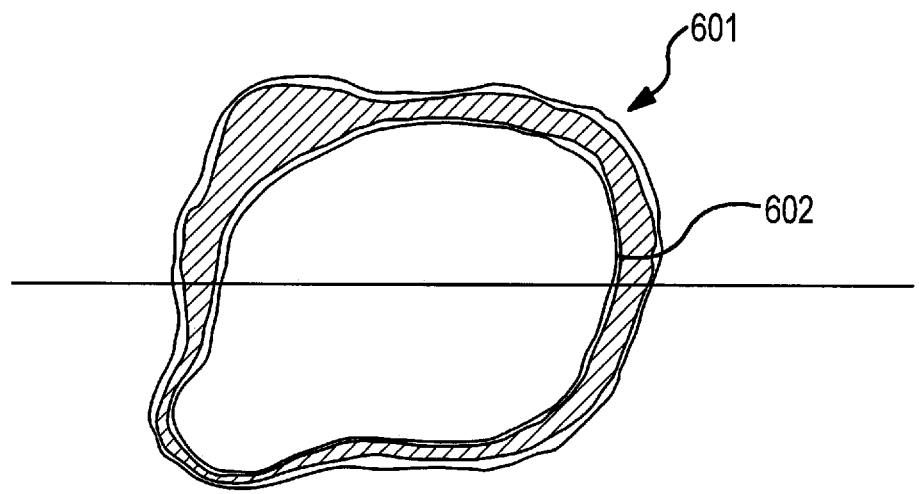
FIG. 4B is a CT slice as taken along section line A of FIG. 2A.
Figure 5A:
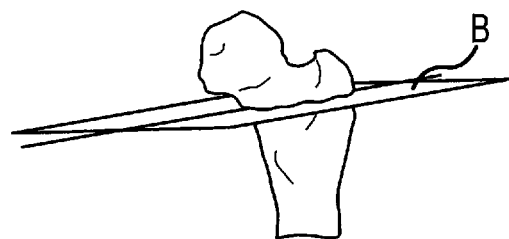
FIG. 5A is a 3D view of the proximal femur of FIG. 2A, illustrating a section line B at which the bone is sectioned during a CT scan to help create a cortical bone model and trabecular bone model.
Figure 5B:
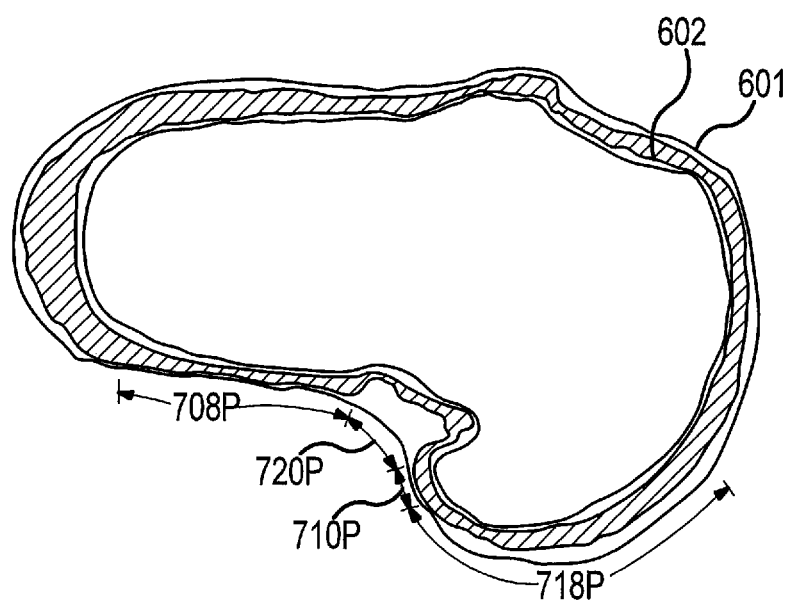
FIG. 5B is a CT slice as taken along section line B of FIG. 5A.
Figure 6A:
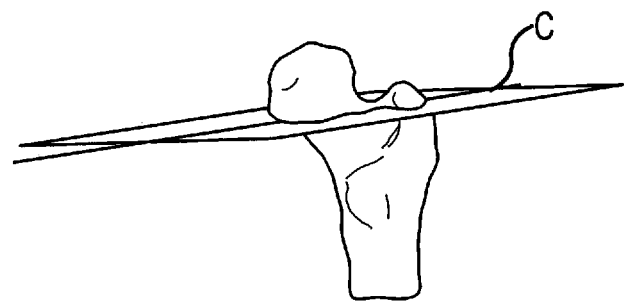
FIG. 6A is a 3D view of the proximal femur of FIG. 2A, illustrating a section line C at which the bone is sectioned during a CT scan to help create a cortical bone model and trabecular bone model.
Figure 6B:
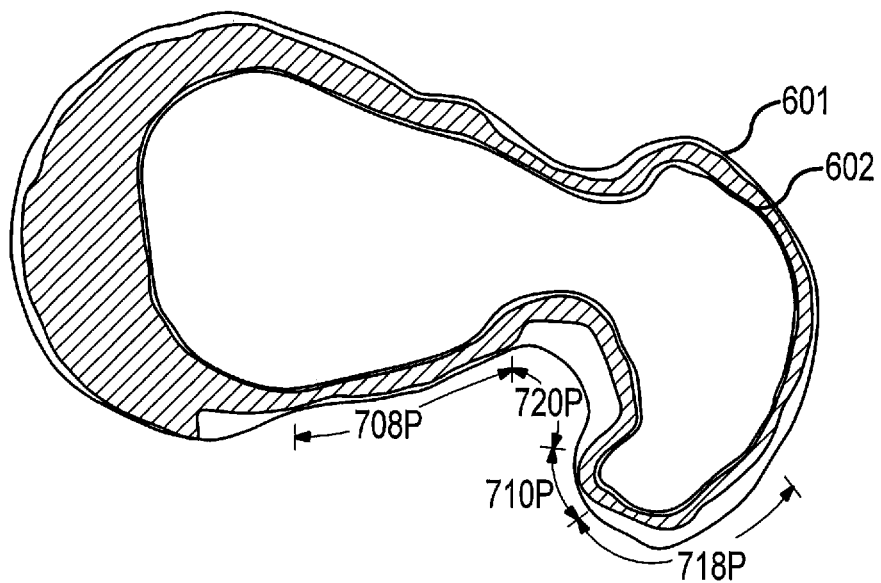
FIG. 6B is a CT slice as taken along section line C of FIG. 6A.

For a discussion of the bone contour lines that may be identified during the image segmentation process, reference is made to FIGS. 4A-6B. FIGS. 4A, 5A and 6A are 3D views of the proximal femur 40 respectively showing section or scan planes A, B and C extending through the femur 40. FIGS. 4B, 5B and 6B are respectively the segmented image slices of planes A, B and C, respectively. As indicated in FIG. 4A, section or scan plane A extends through the proximal femur generally transverse to the femoral axis and just distal of the lesser trochanter. As shown in the resulting segmented image slice depicted in FIG. 4B, the contour line 601 corresponding to the cortical bone and the contour line 602 corresponding to the trabecular bone 602 may be identified.

As indicated in FIG. 5A, section or scan plane B extends through the proximal femur generally transverse to the femoral axis and approximately midway between the tip of the greater trochanter and the lesser trochanter. As shown in the resulting segmented image slice depicted in FIG. 5B, the contour line 601 corresponding to the cortical bone and the contour line 602 corresponding to the trabecular bone 602 may be identified.

As indicated in FIG. 6A, section or scan plane C extends through the proximal femur generally transverse to the femoral axis and just distal the tip of the greater trochanter. As shown in the resulting segmented image slice depicted in FIG. 6B, the contour line 601 corresponding to the cortical bone and the contour line 602 corresponding to the trabecular bone 602 may be identified.

Figure 13:
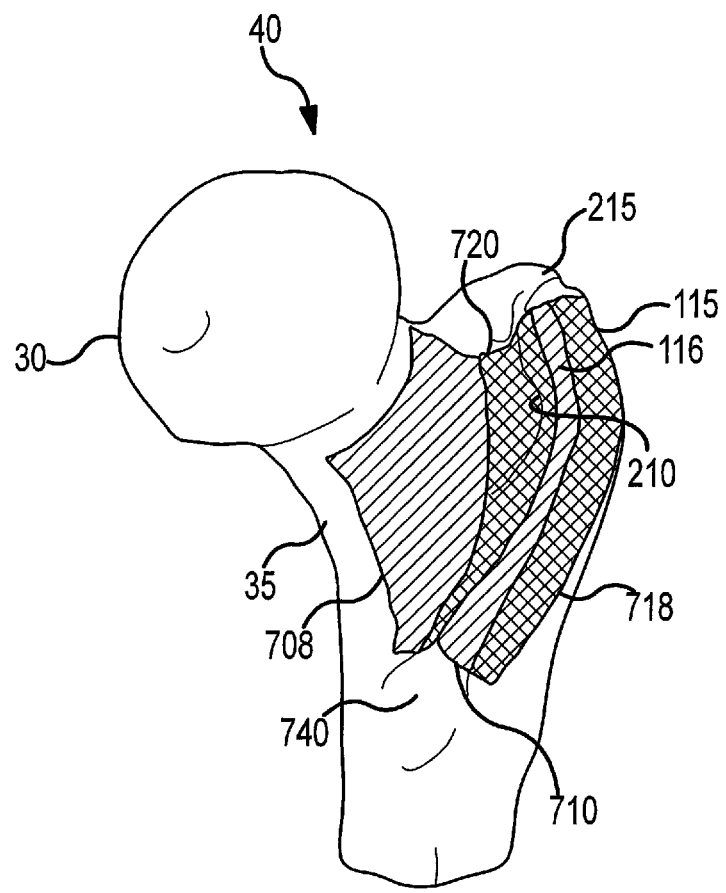
FIG. 13 is a posterior medial view of the proximal femur of FIG. 2A showing the regions of the femur that are mated with the index surfaces of an embodiment of the tool and the regions that correspond to over-estimated or non-contacting surfaces of the tool.

In one embodiment, as can be understood from FIG. 13, the region of the femur 40, which may be matingly received by the tool mating region 20 when the tool 5 is mounted on the femur 40, may include a mating contact surface 708 covering portions of the posterior region of the neck 35 and a mating contact surface 710 that is a narrow band following along the intertrochanteric crest 116. The femur mating contact surfaces 708, 710 may be separated by non-contacting surfaces 718, 720 of the femur 40. The non-contacting surfaces 718, 720 of the proximal femur 40 may include portions 718 of the posterior greater trochanter 115 and portions 720 of the trochanteric fossa 210.

As can be understood from FIGS. 5A, 6A and 13, the portions 708P, 710P of the cortical bone contour lines 601 in FIGS. 5B and 6B correspond to the mating contact surfaces 708, 710 of the femur 40, and the portions 718P, 720P of the cortical bone contour lines 601 in FIGS. 5B and 6B correspond to the non-contact surfaces 718, 720 of the femur 40. As can be understood from FIGS. 4A and 13, the cortical contour line 601 depicted in FIG. 4B is from a slice that would be located below the tool mating regions of the femur 40. Therefore, this contour line 601 depicted in FIG. 4B does not have portions 718P, 720P, 708P, 710P.

As can be understood from FIGS. 5B, 6B and 13, the non-contact portions 718P, 720P of the cortical bone contour lines 601 correspond to surfaces 718, 720 of the femur 40 that are difficult to replicate in the tool mating region 20 due to the extreme variance in surface topography for the surfaces 718, 720. In addition to the difficult to replicate surfaces 718, 720 depicted in FIG. 13, other difficult to replicate surfaces that surfaces portions 718P, 720P may correspond to may include surfaces of osteophytes or other bone surface irregularities. The surface topography variance for the surfaces 718, 720, the osteophytes, etc. may be such that: (1) corresponding regions of the tool mating region 20 would be difficult to machine to correspond to the surfaces 718, 720 of the femur 40 due to limitations in the milling process; or (2) the surfaces 718, 720 would be difficult to model because of limitations in the scanning or 3D computer modeling processes.

The difficult to replicate contour line portions 718P, 720P may be subjected to an overestimation process. Specifically, the difficult to replicate contour line portions 718P, 720P are modified to be extended outwardly away from the interior of the bone (i.e., over-estimated) and, in some instances smoothed with respect to shape. The resulting cortical bone contour lines 601 now include the original portions 708P, 710P in their original shape and location and the now overestimated or outwardly adjusted portions 718P, 720P; these resulting cortical bone contour lines 601 from each image slice are then compiled or reconstructed into the 3D computer generated femur model 1040 used for the preoperative planning process.

The end result of the overestimation process with respect to the manufacture of the completed tool 5 is that the CNC tool paths corresponding to the overestimated regions of the femur model 1040 remove excess materials from the mating region 20 of the blank used to form the tool 5. Accordingly, the tool mating region 20 is configured to matingly contact only with those surfaces 708, 710 of the femur that can be accurately replicated in the tool mating region 20, and those surfaces 718, 720 that cannot be accurately replicated in the tool mating region 20 are not contacted by any surface of the tool mating region 20 because the tool mating region 20 has been over-milled in the areas of the tool mating region 20 corresponding to the difficult to replicate femur surfaces 718, 720. The result is a tool 5 with a mating region 20 that accurately mates to the mating region of the femur 40.

Figure 9A:
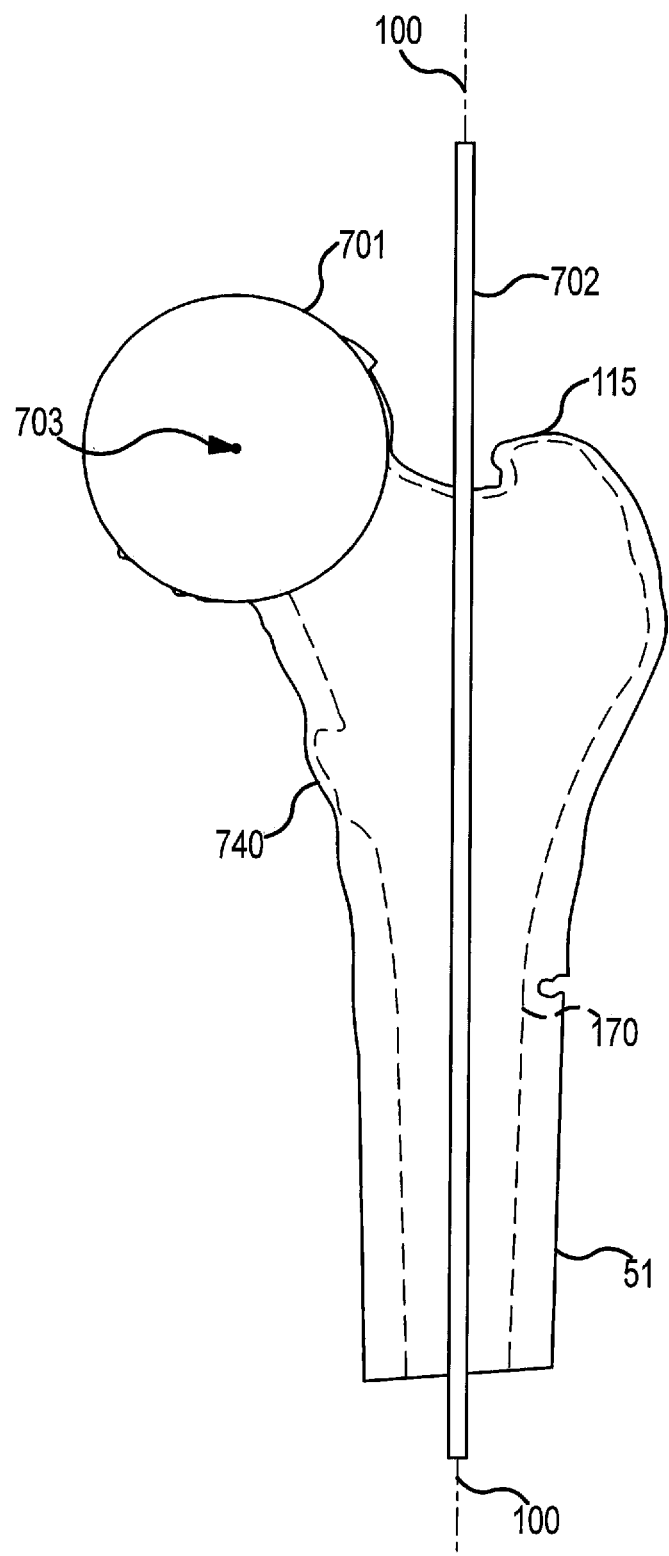
FIG. 9A is a transparent posterior view of a model of the proximal femur of FIG. 2A, wherein a sphere model and a rod model are shown.

In the above-described overestimation process, the line contours 601 for the cortical bone may be subjected to overestimation while the line contours 602 for the trabecular bone are not subjected to overestimation. However, in other embodiments, the contour lines 601, 602 for both the cortical and trabecular bones are subjected to overestimation. The cortical bone contour lines 601 may be employed to generate a 3D computer generated cortical bone model, and the trabecular bone contour lines 602 may be employed to generate a 3D computer generated trabecular bone model. The cortical bone model and the trabecular bone model may be combined into a single 3D computer generated femur model 1040 [block 1501], as depicted in FIG. 9A discussed below. Specifically, as can be understood from FIG. 9A, which is a posterior view of the femur model 1040, once the contour lines are segmented and overestimated as described above, the contour lines may be imported into a 3D computer modeling program. The model program may then be used to generate 3D computer models of the cortical bone 601 and the trabecular bone 602 of the proximal femur 40. The model of the trabecular bone 602 may be subtracted from the model of the cortical bone 601 to create a hollow 3D computer generated femur model 1040, wherein the subtracted model of the trabecular bone 602 creates a hollow region of the femur model 1040 that represents the medullary canal 170.

Overestimation processes are described in more detail in commonly-owned U.S. Patent Application Ser. No. 61/083,053, entitled System and Method for Manufacturing Arthroplasty Jigs Having Improved Mating Accuracy, filed Jul. 23, 2008, which is hereby incorporated by reference in its entirety.

Figure 7:
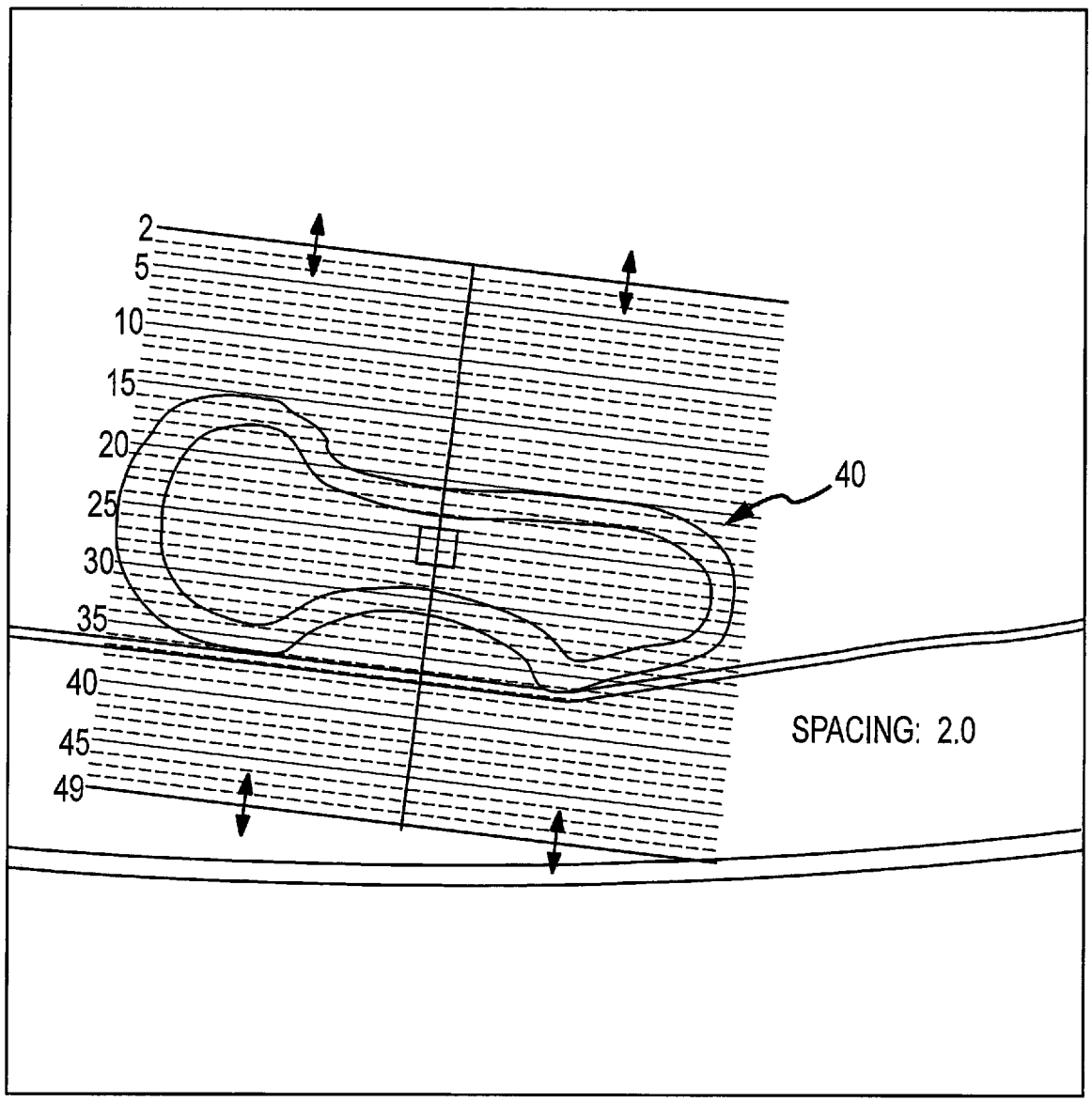
FIG. 7 is an example superior view CT scan of the proximal femur, wherein the correct coronal alignment for CT reconstruction is shown.

When reconstructing the contour lines into the femur model 1040, certain alignments have been found to be advantageous. For example, as indicated in FIG. 7, which is an example superior view CT scan of the proximal femur 40 of FIG. 2A, the CT scan may be reconstructed for proper coronal alignment by causing the coronal slices to be parallel to the femoral neck 35. For this procedure, the slice width and overlap may range from approximately 0.5 mm to approximately 2 mm. In one embodiment, a slice width and overlap of 0.5 mm is used. The DFOV may range between approximately 16 cm to approximately 26 cm field of view. In one embodiment, the reformatted CT scan may include up to one-third of the proximal femur 40, including the femoral head 30 and the lesser trochanter 740. In other embodiments, the CT scan may include a greater or lesser amount of the proximal femur.

Figure 8:
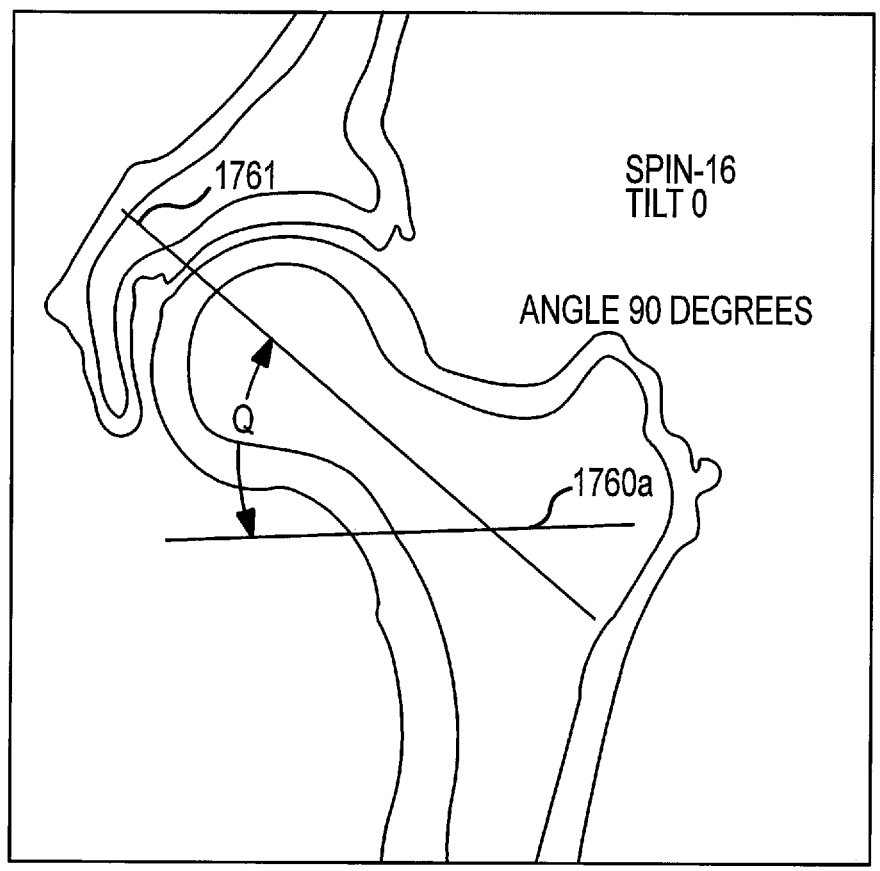
FIG. 8 is an example CT scan of the proximal femur, wherein the correct alignment for the final CT reconstruction is shown.

As indicated in FIG. 8, which is an example CT scan of the proximal femur 40 of FIG. 2A, wherein the proper alignment for the final CT reconstruction is shown from a coronal slice. Specifically, the final reconstruction alignment 1760a is set to an angle Q relative to the long axis 1761 of the femoral neck 35. Angle Q may range from approximately 30 degrees to approximately 60 degrees. In one embodiment, angle Q is 45 degrees. The slice width and overlap may range from approximately 0.5 mm to approximately 2 mm. In one embodiment, the slice width and overlap is 1 mm. The field of view may range from approximately 16 mm to approximately 26 mm. In one embodiment, the scan may include up to one-third of the proximal femur 40, including the femoral head 30 and the lesser trochanter 740. In other embodiments, the CT scan may include a greater or lesser amount of the proximal femur.

V. Preoperative Planning of Tool

As can be understood from FIGS. 1A-1C and the immediately preceding discussion, once the medical images 500 are segmented to identify the bone contour lines 502 [block 1500 and block 1602], the contour lines are overestimated as necessary, and the contour lines are compiled or reconstructed into a 3D model of the femur via a computer modeling program [block 1501], the pre-operative planning process may begin [block 1604], wherein the 3D bone model is utilized to determine: (1) the proper size and placement of a femoral component (e.g. the prosthetic device that will be implanted in the femur); and (2) the location of the resection plane for resection of the femur head and neck, wherein the resection is made to allow for the implantation of the femoral component in the resected femur. The following preoperative planning methods may employ a 3D computer modeling program, such as, for example, Solidworks or Paraview, in the generation, placement, manipulation, determination and importation of various 3D computer models described below.

Figure 9B:
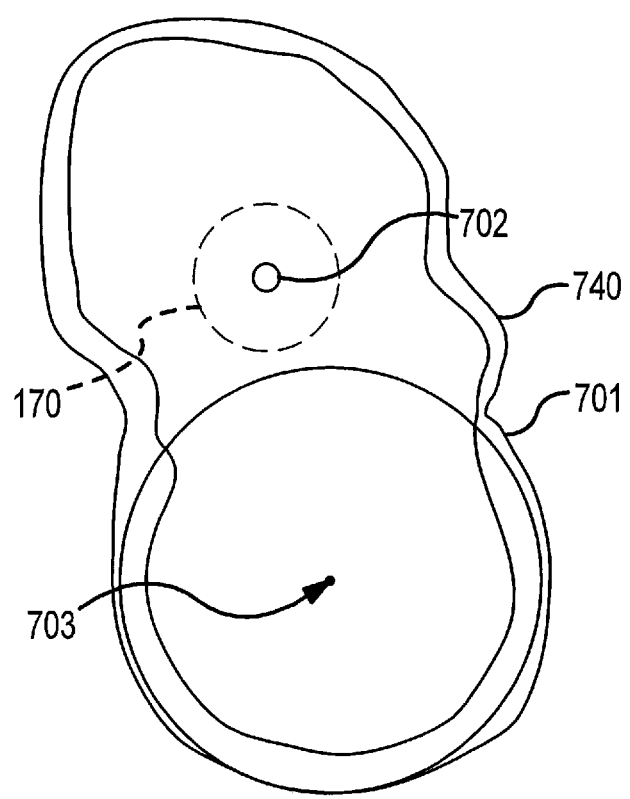
FIG. 9B is a transparent superior view of the models depicted in FIG. 9A.

As can be understood from FIG. 1B and FIGS. 9A and 9B, which are respective transparent posterior and superior views of a 3D computer generated model 1040 of the proximal femur 40 of FIG. 2A, in one embodiment, the preoperative planning may begin with the femur model 1040, a 3D computer generated sphere model 701, and a 3D computer generated rod model 702 being imported into a modeling space [block 1502]. As can be understood from FIGS. 9A and 9B, the femur model 1040, which is a result of the compiled or reconstructed contour lines, some of which may have been overestimated, may have a head 30, a neck 35, a shaft 51, a greater trochanter, and an medullary canal 170.

As indicated in FIGS. 9A and 9B, the models 701, 702, 1040 are combined together in a superpositioned arrangement. Specifically, the rod model 702 may be positioned so that it generally aligns with the center of the medullary canal 170 of the shaft of the femur model 1040, which generally corresponds to a central axis 100 of the shaft of the femur. In other words, the rod 702 may be positioned to be generally coaxial with the femur axis 100.

The sphere model 701 may be positioned so the centers of the sphere 701 and head 35 are located at the same point. The diameter of the sphere model 701 may be increase or decreased to cause the sphere model 701 to generally approximate the femoral head 30 such that the hemispherical surfaces of the head 30 and the sphere 701 are generally coextensive for a significant portion of the hemispherical surface of the head 30. Generally, if there is damage to the head 30, the damage is typically to the superior and anterior surfaces, so the sphere 701 is typically positioned and sized such that hemispherical surface of the sphere 701 is generally coextensive with the inferior and posterior regions of the head 30. Once the sphere 701 is properly placed and sized, the center 703 of the sphere 701 will generally approximate the center of the hip joint. The proper positioning and sizing of the models 701, 702 can be verified by looking at both posterior (FIG. 9A) and superior (FIG. 9B) views.

Figure 9C:
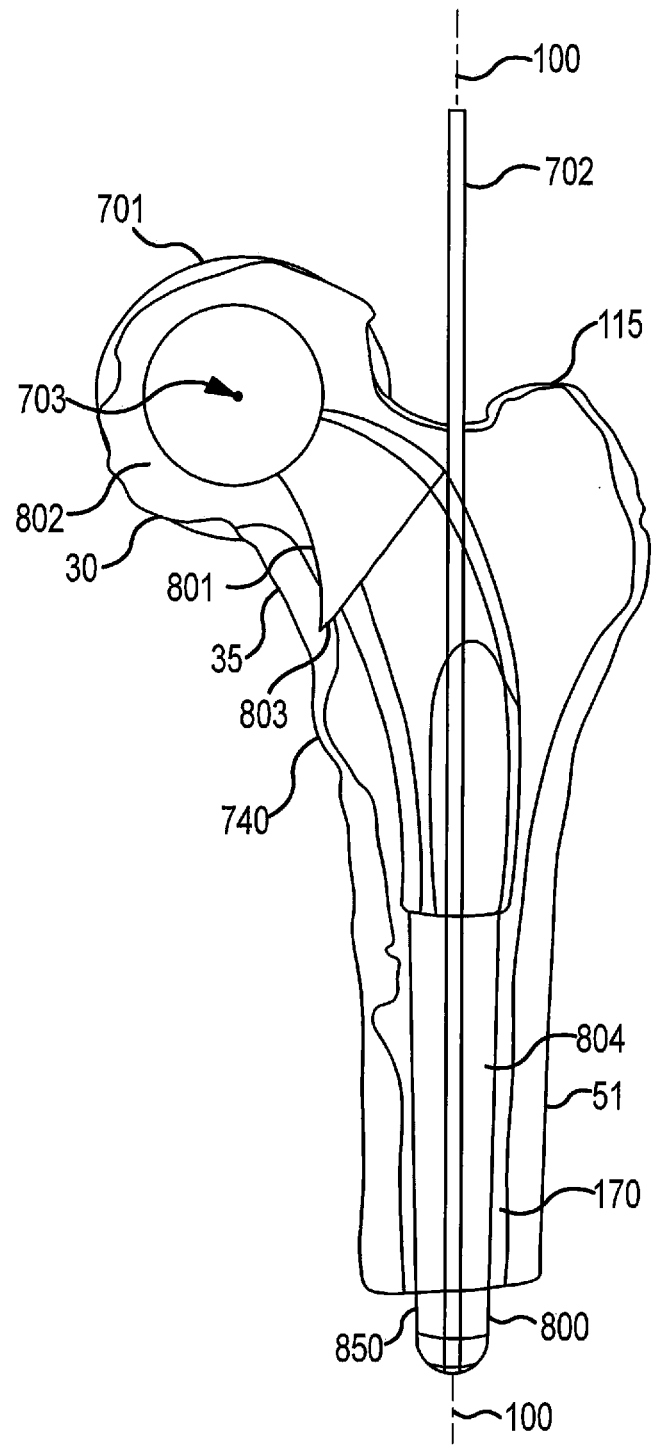
FIG. 9C is the same view as FIG. 9A, except a femoral component model is also shown.

As can be understood from FIG. 1B and FIG. 9C, which is the same view as FIG. 9B, except with a femoral component model 850 depicted with the other models 701, 702, 1040, a 3D computer generated femoral component model 850 may be imported into the modeling space [block 1503]. The femoral component model 850 may include a shaft 804, a head 802 and a spacer region 801. The spacer region 801 may have a surface 803 that abuts against the surface of the bone resection when the actual implant is properly and fully implanted in the resected femur. The 3D femoral component model 850 may be selected from a database of femoral component models, the models in the data base corresponding to the sizes of femoral components available from a selected manufacturer. Size selection is based on the shape and size of the medullary canal 170. Once the position of the neck resection has been determined, the largest component that fits within the canal is chosen.

The sphere model 701 and rod model 702 are used to plan the proper alignment and placement of the femoral component model 850. Specifically, the femoral component model 850 may be superimposed with the rest of the models 701, 702, 1040 such that the long axis of the shaft 804 of the component 800 generally corresponds to the long axis of the rod 702 in a generally coaxial manner, and the center of the head 802 of the component model 850 generally corresponds to the approximated hip joint center 703. To properly position the component model 850, the size and the shaft to neck angle of the spacer 801 may be adjusted according to the ranges available from the manufacturer for the femoral component.

The above-described embodiment superimposes the sphere and rod models 701, 702 on the femur model 1040 prior to superimposing the femoral component model 850 and using the sphere and rod model locations to position and size the femoral component model 850. However, in other embodiments, the femoral component model 850 may be superimposed on the femur model 1040 for positioning and sizing without the presence and use of the sphere and rod models 701, 702.

Figure 10:
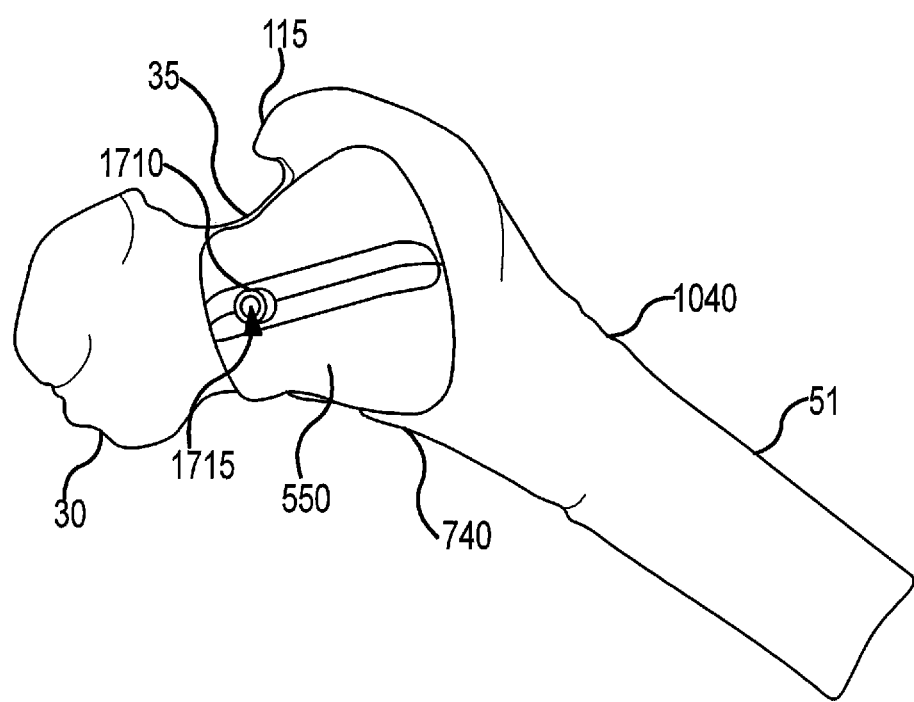
FIG. 10 is an isometric posterior view of a model of the femur of FIG. 2A, wherein the surgical guide tool blank model is shown positioned on the femur.

As can be understood from FIGS. 1B and 1C and FIG. 10, which is an isometric posterior view of the femoral model 1040 of FIG. 9C, except with the other models 701, 702, 850 hidden for clarity purposes, a 3D computer generated tool blank model 550 is generated [block 1504] and imported into the modeling space to be superpositioned with the femoral model 1040 to define the mating region 20 and saw guide 1725 in the tool blank model 550 [block 1505 and 1606]. In one embodiment for a posterior approach surgical procedure, the tool blank model 550 is positioned over the posterior surface of the femur model 1040 such that: (1) the surfaces of the femur model 1040 corresponding to the mating contact surfaces 708, 710 and non-contact surfaces 718, 720 of the femur 40, as discussed in detail below with respect to FIG. 13, are covered by the tool 5; and (2) the head 30 of the femur model 1040 is exposed.

Figure 11:
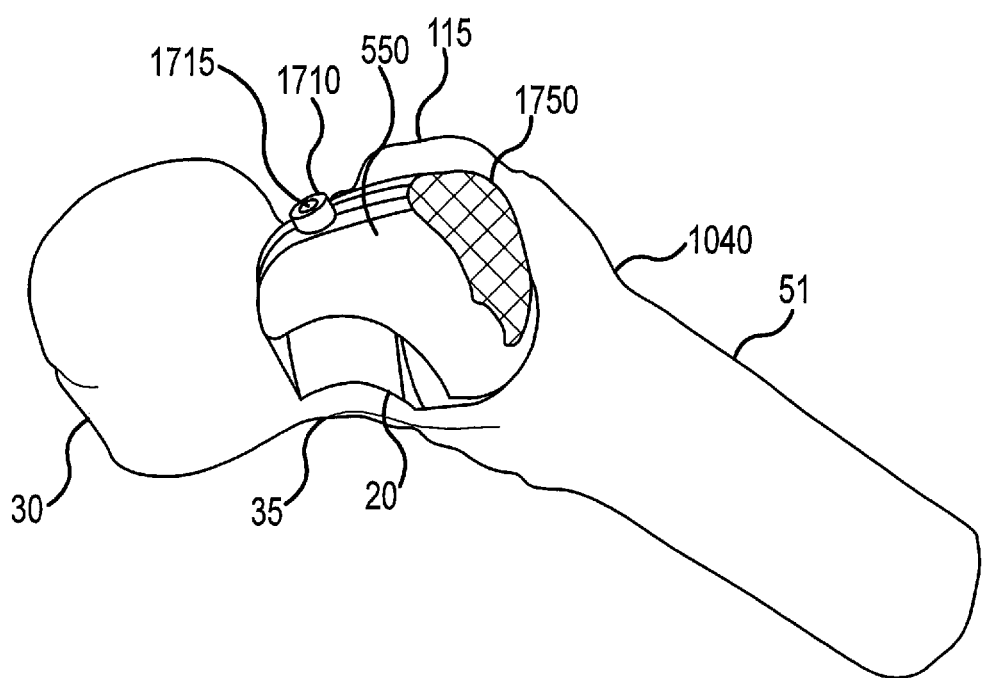
FIG. 11 is an isometric inferior-posterior view of the model of the femur and the surgical guide tool blank model, wherein the distal end of the tool model is highlighted to illustrate a portion of the tool that may be removed for proper exposure of the greater trochanter.

As shown in FIG. 11, which is a inferior-posterior isometric view of what is depicted in FIG. 10, a distal portion 1750 of the tool blank model 550 may be removed to provide a non-contacting arrangement between the resulting tool 5 and non-mating regions of the proximal femur 40, such as those regions near the greater trochanter 115.

Figure 12:
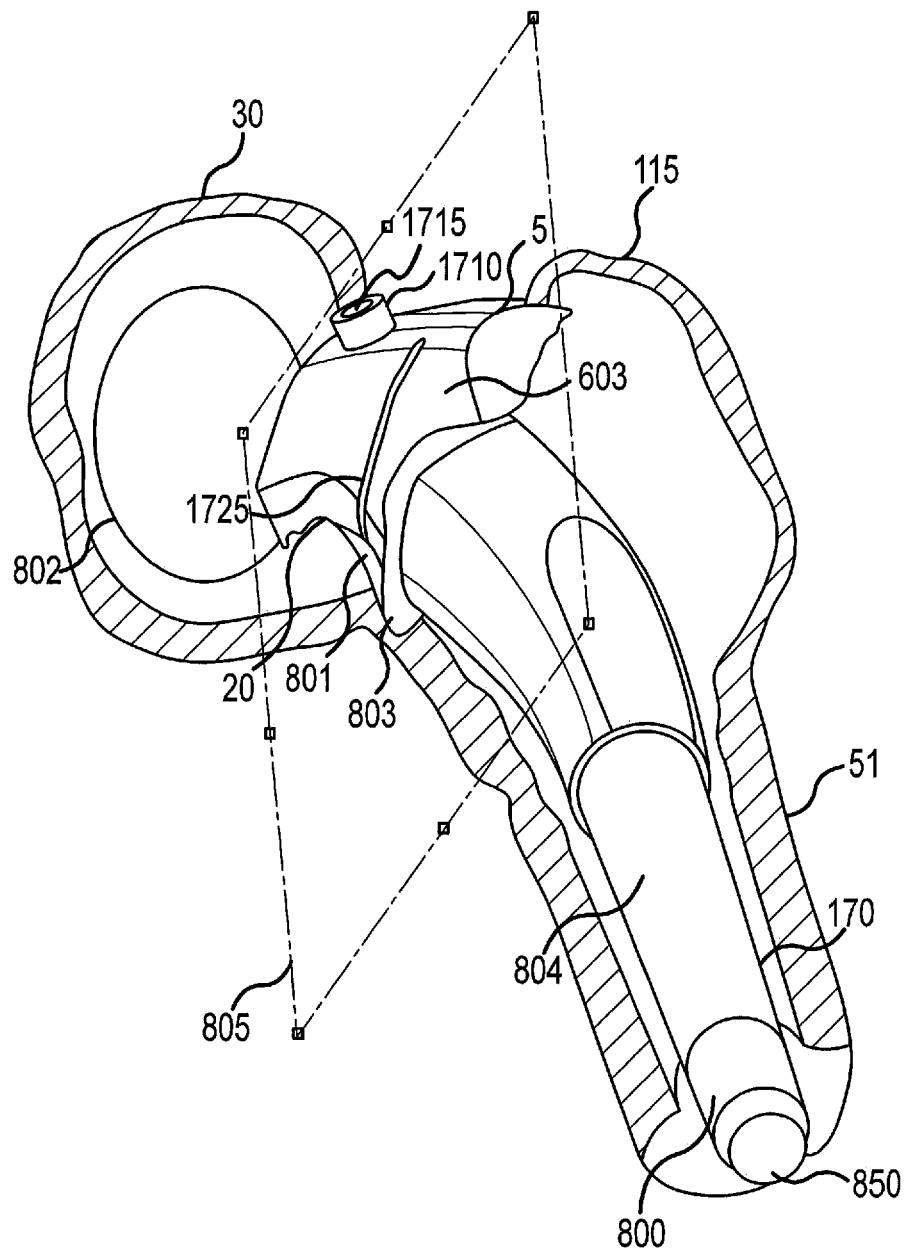
FIG. 12 is a transparent view of the femoral component model, model of the femur, and the model of the customized surgical guide tool properly superimposed relative to each other.

As can be understood from FIGS. 1B and 1C and FIG. 12, which is generally the same view as FIG. 11, except the femoral component model 850 is visible and the tool blank model 550 is now a customized tool model 603, once the tool blank model 550 is properly positioned on the femur model 1040, the tool mating region 20 and saw guide 1725 may be defined and imported into the tool blank model 550 to create the tool model 603 [block 1506 and block 1606]. Specifically, those mating contact surfaces 708a, 710a and non-contacting surfaces 718a, 720a of the tool mating region 20 that respectively correspond to the contact surfaces 708, 710 and non-contact or overestimated surfaces 718, 720 of the femur 40 of FIG. 13 are identified on the surface of the femur model 1040 and imported or otherwise used to define the contacting surfaces 708a, 710a and non-contacting surfaces 718a, 720a in the mating region of the tool blank model 550. As can be understood from FIG. 1B, in one embodiment, the contacting surfaces 708, 710 and non-contacting surfaces 718, 720 of the femur model 1040 may be identified and defined as 3D surface models 537, 539 or other types of "data" that are imported into the tool blank model 550 to create the contacting surfaces 708a, 710a and non-contacting surfaces 718a, 720a in the mating region of the tool blank model 550 [block 1506].

As can be understood from FIG. 12, since the femoral component model 850 is properly positioned in the femur model 1040 in a manner that is predicted to give a desirable surgical outcome for the hip implantation, the surface 803 of the spacer region 801 of the component model 850 may be coplanar to the resection plane 805 needed to allow the actual implanted femoral component to achieve the implant positioning that will achieve the predicted desirable surgical outcome. In other words, the spacer region surface 803 will correspond to the position and orientation of the resection plane 805 when the component model 850 is properly positioned in the femur model 1040. Thus, the position and orientation of the spacer region surface 803 may be used to define the position and orientation of the resection plane 805 and, as can be understood from FIG. 1B, a resection plane model 538 or other types of "data" may be defined and imported into the tool blank model 550 to define the saw guide 1725 in the tool blank model 550 [block 1506]. Since the location and orientation of the surface models 539, 537 and plane model 538 may be referenced relative to each other due to the femur, component and blank models 1040, 805, 550 being superimposed with each other, the position and orientation relationships are maintained in the resulting tool model 603 [block 1507]. Thus, for the resulting tool model 603 and tool 5 manufactured therefrom, the saw guide 1725 may be positioned and oriented relative to the customized mating or indexing region 20 such that, when the mating surfaces 708a, 710a of the mating region 20 matingly contact the bone surfaces 708, 710 when the tool mating region 20 matingly receives therein the region of the femur 40 having the bone surfaces 708, 710, the saw guide 1725 may be oriented over the femur neck 35 such that the saw guide 1725 corresponds with a desired resection plane 805 through the femoral neck 35 that was identified during the preoperative planning. In other words, the cavity or mating region 20 of the tool 5 conforms to the segmented CT scans or MRI scans, overestimated as necessary, of the patient's femur, and the saw guide 1725 is positioned so as to result in a preoperatively planned resection of the proximal femur when the tool mating region 20 matingly engages the proximal femur and a sawing action is guided by the saw guide 1725.

Proper alignment of the saw slot 1725 with the preoperatively planned resection plane exposes the femoral neck to provide a properly oriented surface for proper alignment of the femoral component. A properly positioned femoral component prevents or at least minimizes the chances of several undesirable complications. For example, an improperly positioned femoral component can cause a change of leg length, dislocation of the hip or perforation of the femur.

As can be understood from FIGS. 1A-1C, once the tool model 603 is defined, the tool model 603 may be used to generate automated manufacturing instructions (e.g., tool paths, etc.). The tool model 603 or automated manufacturing instructions are sent to the CNC machine 10 from the preoperative planning system 6 [block 1508], and the actual tool 5 is manufactured from an actual tool blank 50 via the CNC machine 10 [block 1608]. The finished tool 5 may be marked with patient data (e.g., name, hip identification, etc.), surgeon name, medical facility name, or other information. The tool 5 may then be sterilized, packaged and sent to the surgeon [block 1610].

During surgery, the surgeon may fit the tool appropriately on the femur and, in one embodiment, drill into the hole 1715 of the fastener feature 1710 at the top side 1755 of the tool and insert a fastening member 1716 to stabilize the tool [block 1612]. In some embodiments, the tool 5 may be held in place by the surgeon or other medical personnel. Once positioned, the surgeon may place a saw blade through the saw slot 1725 and prepare to saw through the resection plane to make at least a partial head and neck resection [block 1614]. Once the resection is at least partially complete, the tool may be discarded [block 1616]. In some embodiments, the tool 5 may remain in place until the resection is complete.

The surgeon may then further prep the resected proximal femur and then implant the femoral component 800 in a manner that replicates the preoperative planning such that the surface 803 abuts against the resection surface of the femur. As the size selection and positioning of the femoral component are determined via computer modeling during the preoperative planning process, and the tool 5 is custom configured to facilitate the preoperatively planned positioning of the femoral component, the tool 5 disclosed herein facilitates FIRS that is substantially more likely to result in a positive surgical outcome for the patient as compared to conventional methods that rely on x-rays, hand measuring techniques and surgeon visual assessment. In other words, the tool 5 decreases the risks commonly associated with an improperly placed femoral component in total hip replacement surgery, such as dislocation of the hip, a change in the length of the leg or perforation of the femur.

As the surgical planning is integrated into the tool 5 prior to the time of surgery, the surgical time is substantially reduced because the surgeon simply has to cause the tool 5 to engage the proximal femur, as opposed to determining the proper location for the resection based off of visual inspection at the time of surgery. Thus, the tool 5 aids the surgeon in accurately and quickly placing the femoral component 800. In other words, the tool 5 also decreases the risks associated with the length of the surgical time, such as, infection, excessive bleeding, etc.

In one embodiment and to a greater or lesser extent, the above-described POP procedure is a manual process, wherein computer generated 3D models 701, 702, 1040, 850 are manually manipulated relative to each other by a person sitting in front of a computer 6 and visually observing the 3D models 701, 702, 1040, 850 on the computer screen 9 and manipulating the 3D models 701, 702, 1040, 850 via the computer controls 11. In other embodiments and to a greater or lesser extent, the POP process is generally or completely automated. For example, a computer program may manipulate computer generated 3D models 701, 702, 1040, 850 relative to each other to preoperatively plan the tool 5. In some embodiments, the above-described POP process may have portions that are generally manual while other portions that are generally automated.

VI. Candidate Contact and Non-Contact Surfaces of Proximal Femur

As described in detail above, the mating region 20 of the tool 5 may be customized based on a patient's individual bone shape. The tool 5 may be machined, molded or otherwise formed from the non-customized state as illustrated in FIGS. 2B-2E to a customized state as indicated in FIGS. 2F-2H, based on a patient's individual bone scan, for example an MRI scan or CT-scan. For example, the bone scan data may be utilized to generate a 3D computer generated model 1040 of the patient's proximal femur 40. A 3D computer generated model 550 of the blank of the tool 5, the 3D femur model 1040, and 3D computer generated models of the implant component 850, the sphere 701, and the rod 702 may be superimposed and aligned as described above to preoperatively plan the patient specific tool 5. That is, through the information received from the MRI scan or CT-scan and the computer modeling, the tool 5 may be customized at the mating region 20 such that the tool 5 will have mating or indexing surfaces 708a, 710a of the mating region 20 that generally conform to the predetermined specific surface geometry of the patient's own proximal femur 40. In some embodiments, the predetermined specific geometry will be that of surfaces 708, 710 discussed with respect to FIG. 13, which is a posterior medial view of the proximal femur 40 of FIG. 2A showing the surfaces 708, 710 of the femur 40 that are mated with the index surfaces 708a, 710a of the tool mating region 20 and the surfaces 718, 720 that correspond to over-estimated or non-contacting surfaces 718a, 720a of the tool mating region 20.

In one embodiment, the femur mating region depicted in FIG. 13 may be applicable to a posterior approach to help with stable positioning of the tool 5 on the femur 40. As shown in FIG. 13, a first mating surface 708 covers portions of the posterior region of the neck 35, starting medially between approximately 1 mm and approximately 5 mm after the cartilage covering the head 30 of the femur 40 terminates laterally and laterally extends between approximately 15 mm and approximately 35 mm to or towards the trochanteric fossa 210. The inferior boundary of surface 708 may terminate approximately 5 mm superior to the inferior border between the posterior and anterior surfaces of the neck 35, or may extend up to approximately 5 mm anterior past this border. The superior boundary of mating surface 708 may extend approximately 0 mm to approximately 5 mm posterior to the superior junction between the posterior surface and the anterior surface of the neck 35. A second mating surface 710 may be a narrow band measuring between approximately 0.5 mm and approximately 12 mm medial-lateral. The second mating surface 710 may follow along the intertrochanteric crest 116. Mating surface 710 may begin approximately 0 mm to approximately 12 mm superior to the lesser trochanter 740 and may extend approximately 0 mm to approximately 18 mm inferior to the most superior tip 215 of the posterior surface of the greater trochanter 115. These mating surfaces 708, 710 of the femur 40 may be used to define the mating contact surfaces 708a, 710a of the tool mating region 20 (see FIG. 2G) such that the tool contact surfaces 708a, 710a may matingly contact the femur surfaces 708, 710 when the tool mating region 20 mating receives or engages the femur 40 as depicted in FIG. 2H.

The non-mating surfaces 718, 720 of the femur 40, which are spanned in a spaced-apart or non-contacting arrangement by corresponding non-contacting surfaces 718a, 720a of the tool mating region 20, as depicted in FIG. 2H, are also depicted in FIG. 13. A first non-mating surface 718 may include portions of the posterior greater trochanter 115 and extend superior-inferior adjacent the intertrochanteric crest 116. The medial boundary of the first non-mating surface 718 may be the second mating surface 710, and may extend medial-lateral approximately 0 mm to approximately 12 mm. The second non-mating surface 20 may span portions of the trochanteric fossa 210, and may have a medial boundary that is the first mating surface 708 and a lateral boundary that is the second mating surface 710, and a medial-lateral width that may vary between approximately 0 mm and approximately 20 mm. Both the first non-mating surface 718 and the second non-mating surface 720 may have inferior-superior dimensions similar to the first mating surface 708 and the second mating surface 710.

As discussed in detail above, during segmentation, contour line portions corresponding to non-mating surfaces 718, 720 and osteophytes may be overestimated (e.g., moved outward from the interior of the bone and smoothed) such that portions of the tool mating region 20 defined according to those overestimated contour line portions are over-machined, ensuring that little or no contact occurs between the resulting non-mating surfaces 718a, 720a of the tool mating region 20 (see FIG. 2G) and the corresponding non-mating surfaces 718, 720 of the bone when the tool mating region 20 matingly receives the region of the femur 40 having the non-mating surfaces 718, 720, as shown in FIG. 2H.

As just discussed with respect to FIG. 13, in one embodiment, the femur 40 may include contact surfaces 708, 710 and non-contact surfaces 718, 720 such that a tool 5 configured for a posterior approach may have a mating region 20 configured to have corresponding mating contact surfaces 708a, 710a and non-contacting surfaces 718a, 720a, as indicated in FIGS. 2G and 2H. In other embodiments, the tool mating region 20 may be such that the mating contact and non-contact surfaces of the tool mating region 20 are configured to correspond to mating and non-contact surfaces of other regions of the femur 40 as described below with respect to FIGS. 14A-14B, 15 and 16A-16B.

Figure 14A:
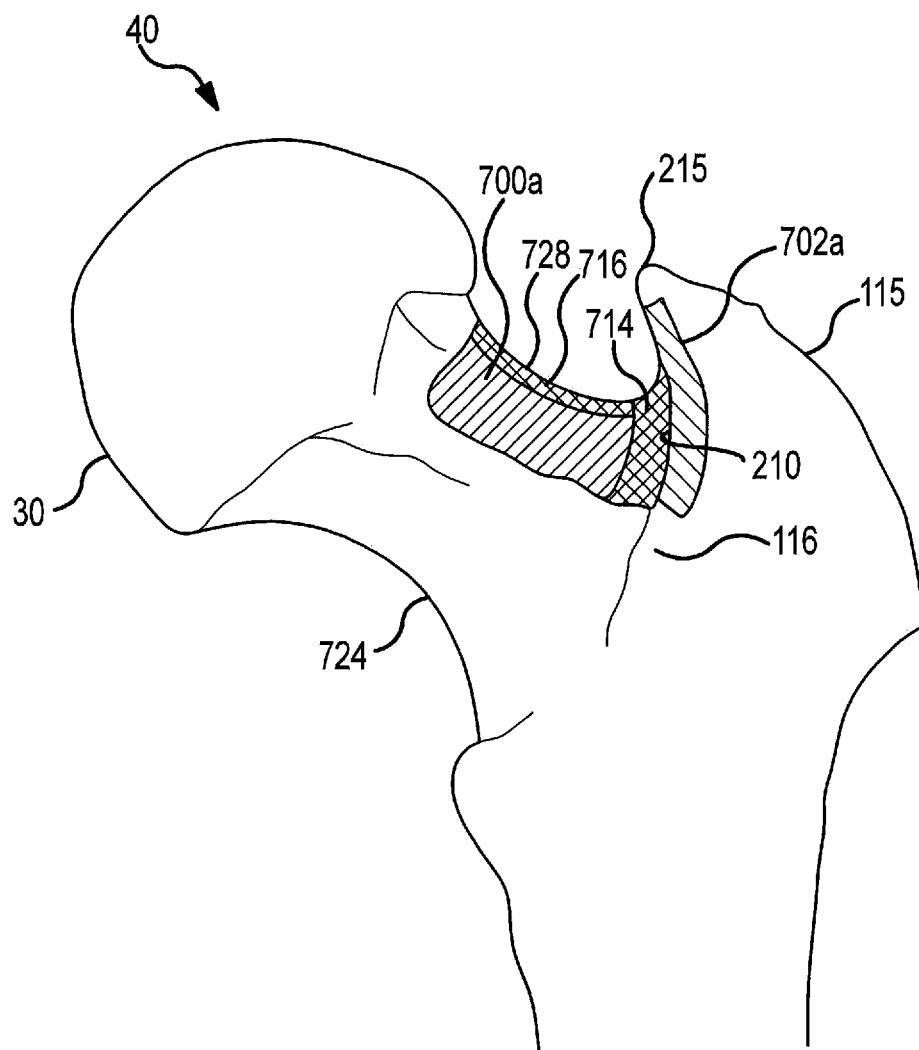
FIGS. 14A-14B are, respectively, posterior and anterior views of the proximal femur, wherein the mating region of the femur may be appropriate for a posterior or anteriorlateral surgical approach.
Figure 14B:
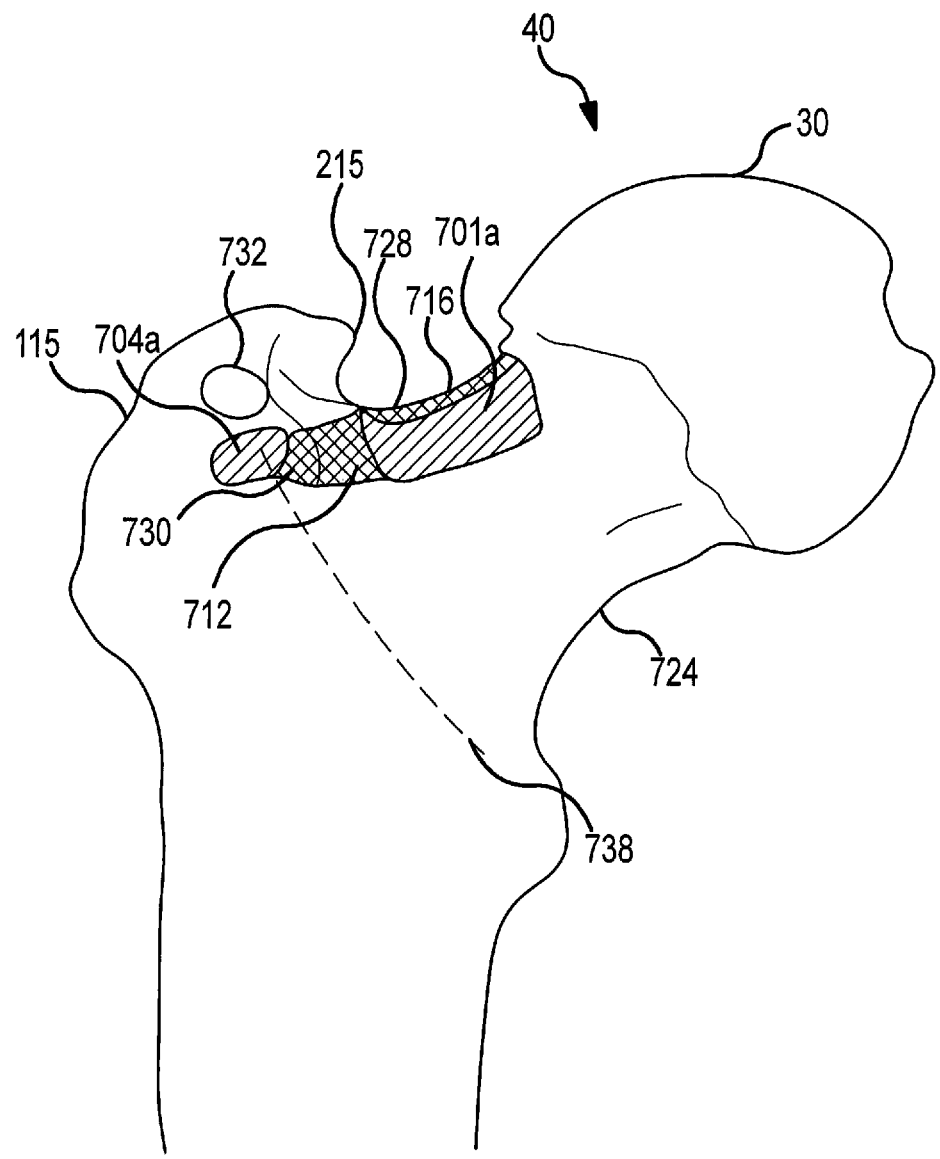

As shown in FIGS. 14A-14B, which are, respectively, posterior and anterior views of the proximal femur 40, the mating region of the femur 40 may be appropriate for a posterior or anteriorlateral surgical approach. For example, the mating region of the femur 40 may include mating surfaces 700a, 701a, 702a, 704a. As can be understood from FIG. 2I, which is a view similar to FIG. 2G, except of a tool mating region 20 configured to matingly engage the mating surfaces 700a, 701a, 702a, 704a depicted in FIGS. 14A-14B, the mating surfaces 700a, 701a, 702a, 704a of the femur 40 may be matingly contacted by corresponding mating or index contact surfaces 700b, 701b, 702b, 704b of the tool mating region 20 to help stabilize the positioning of the tool 5 on the femur 40. In other words, like the tool mating region 20 depicted in FIG. 2G is configured to matingly engage the mating surfaces of the femur 40 depicted in FIG. 13, the tool mating region 20 depicted in FIG. 2I is configured to matingly engage the mating surfaces of the femur 40 depicted in FIGS. 14A-14B.

As indicated in FIGS. 14A-14B, a first mating surface 700a includes portions of the posterior region 724 of the neck 35, having a medial starting point between approximately 1 mm and approximately 5 mm after the cartilage covering the femoral head 30 terminates laterally and extends laterally between approximately 15 mm and approximately 35 mm to or towards the trochanteric fossa 210. The inferior border of the first mating surface 700a begins approximately midway superiorly-inferiorly along the intertrochanteric crest 116, and follows the long axis of the neck 35. The superior border of the first mating surface 700a is between approximately 1 mm and approximately 3 mm below the superior junction 728 between the posterior and anterior surfaces of the neck 35. A second mating surface 701a has approximately the same medial-lateral width as section 700a, but may terminate before the tubercle 730 of the femur 40. The superior border of the second mating surface 701a is approximately 1 mm to approximately 3 mm below the superior junction 728 between the posterior and anterior surfaces of the neck 35. The inferior-superior distance of second mating surface 701a is between 5 and 10 mm. A third mating surface 702a is a narrow band, measuring generally medial-lateral between approximately 0.5 mm and approximately 8 mm, that follows along the intertrochanteric crest 116. Mating surface 702a begins approximately midway superior-inferior along the intertrochanteric crest 116 and may extend any length greater than approximately 5 mm to or towards the most superior tip 215 of the posterior surface of the greater trochanter 115. A fourth mating surface 704a lies on the anterior greater trochanter 115, lateral to the tubercle 730 of the femur 40, and inferior to the origin of the obturator internus 732. The medial-lateral distance of mating surface 704a measures between approximately 3 mm to approximately 14 mm, and its inferior-superior distance measures between approximately 3 mm to approximately 10 mm.

Figure 2I:
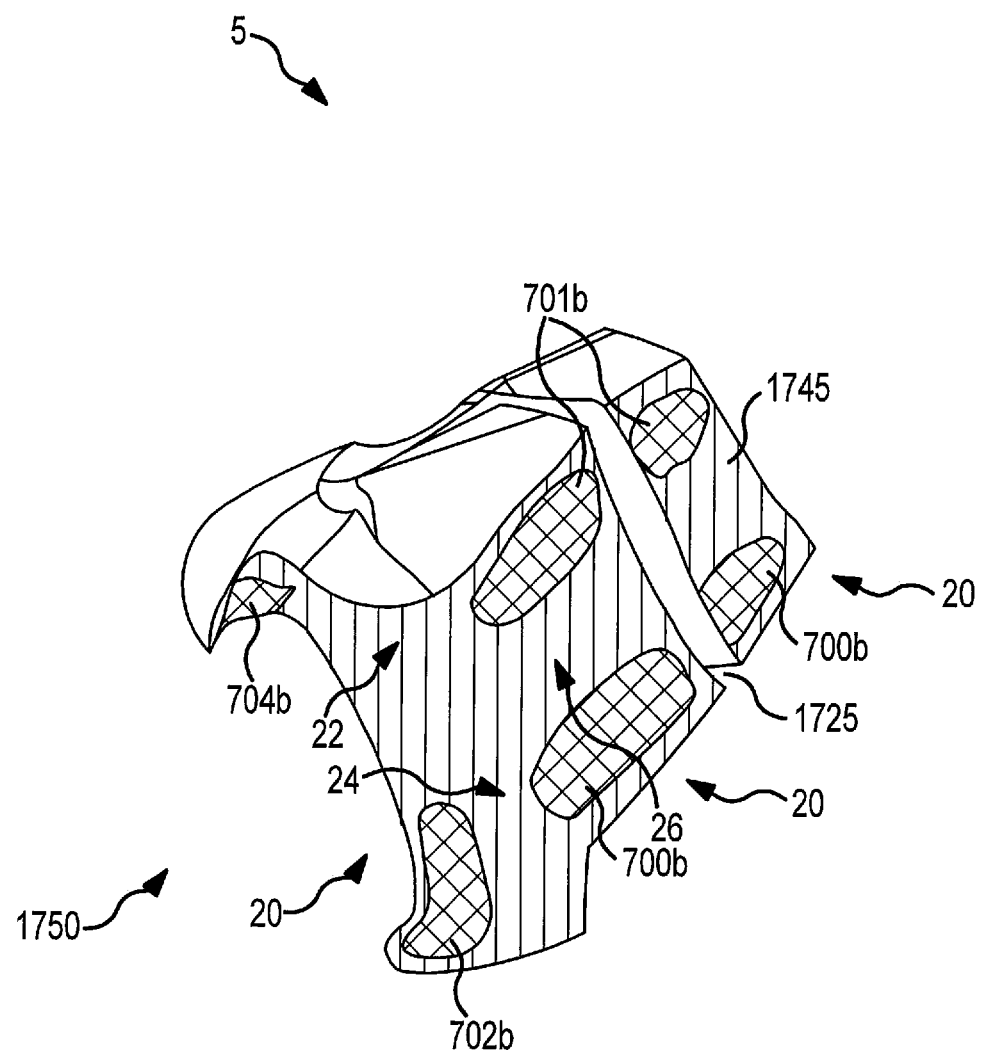
FIG. 2I is a view similar to FIG. 2G, except of a tool with a mating region configured to matingly engage the mating region of the femur depicted in FIGS. 14A-14B.

As indicated in FIGS. 14A-14B, mating surfaces 700a, 701a, 702a, 704a may be separated by non-mating surfaces 712, 714, 716 that are spanned by and correspond respectively with non-contacting surfaces 22, 24, 26 of the mating region 20 of the tool 5 (see FIG. 2I). A first non-mating surface 712 may include portions of the tubercle 730 of the femur 40. A second non-mating surface 714 may span portions of the trochanteric fossa 210. A third non-mating surface 716 may contain the superior junction 728 between the posterior and anterior surfaces of the neck 35, and may be between approximately 1 mm to approximately 5 mm anterior-posterior. In a manner similar to that described above with respect to the non-contact surfaces 718a, 720a of the tool mating region 20 depicted in FIGS. 2G-2H, during segmentation, contour line portions corresponding to non-mating surfaces 712, 714, 716 may be overestimated (e.g., moved outward from the interior of the bone and smoothed) such that portions of the tool mating region 20 defined according to those overestimated contour line portions are over-machined, ensuring that little or no contact occurs between the resulting non-mating surfaces 22, 24, 26 of the tool mating region 20 (see FIG. 2I) and the corresponding non-mating surfaces 712, 714, 716 of the femur 40 when the tool mating region 20 matingly receives the region of the bone having the non-mating surfaces 712, 714, 716.

Figure 2J:
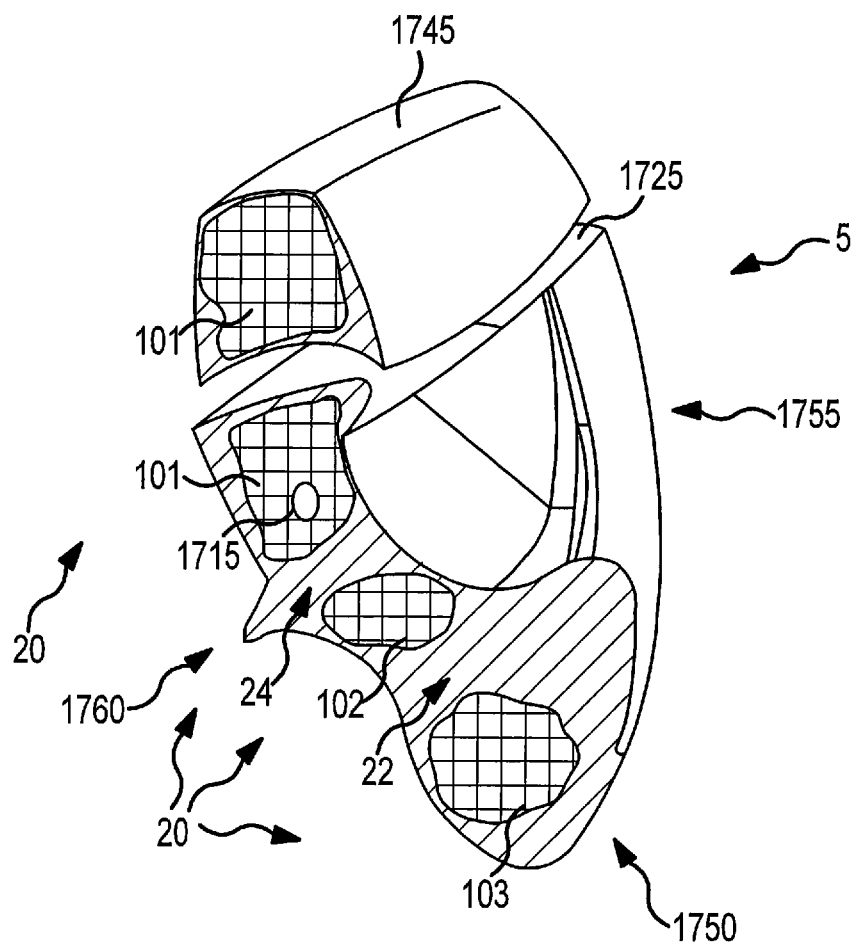
FIG. 2J is the same view as 2G, except of a tool with a mating region configured to matingly engage the mating region of the femur depicted in FIG. 15.
Figure 15:
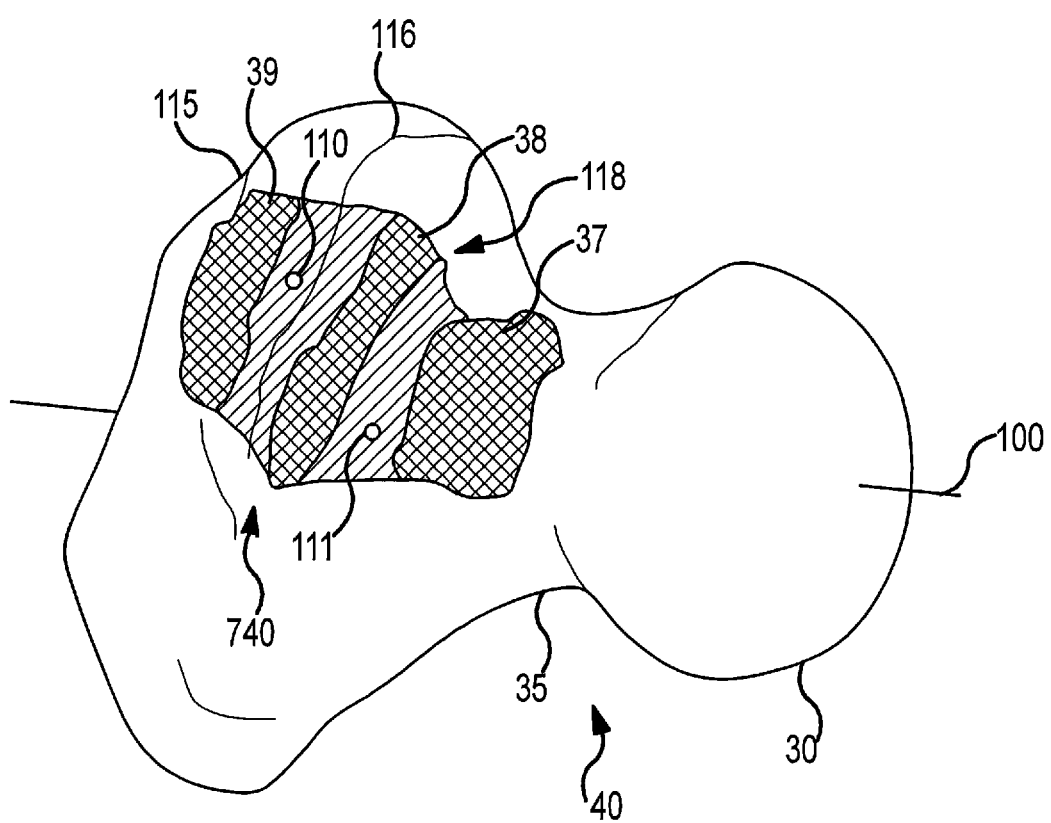
FIG. 15 is an isometric posterior view of the proximal femur and illustrates yet another mating region of the femur that may be used to define the mating region of another embodiment of the tool configured for a posterior surgical approach.

FIG. 15, which is an isometric posterior view of the proximal femur 40, illustrates yet another mating region of the femur 40 that may be used to define the mating region 20 of another embodiment of the tool 5. As can be understood from FIG. 15 and FIG. 2J, which is the same view as 2G, except of a tool 5 with a mating region 20 configured to matingly engage the mating region of the femur 40 depicted in FIG. 15 instead of the mating region of the femur 40 depicted in FIG. 13, the tool mating region 20 may be adapted to receive therein and mate with surfaces of the proximal femur 40, such as, for example, the posterior region 37 of the neck 35, a medial posterior surface 38 of the greater trochanter 115 between the intertrochanteric crest 116 and trochanteric fossa 118, and a region 39 that is part of the lateral posterior greater trochanter 115 and the lateral posterior body of the femur bordering the lateral side of the intertrochanteric crest 116. More specifically, the mating surface 37 may cover portions of the posterior region of the neck 35, starting medially between approximately 1 mm and approximately 5 mm after the cartilage covering the head 30 of the femur 40 terminates laterally and laterally extends between approximately 15 mm and approximately 35 mm to or towards the trochanteric fossa 118. Region 38 may be a band, extending from the lesser trochanter 740 to the anterior surface of the femur, and ranging in width from between approximately 0 mm to approximately 14 mm. The medial border of region 38 is the trochanteric fossa 118 and the lateral border is approximately the intertrochanteric crest 116. Region 39 begins medially at approximately the crest 116, and may extend from 0 mm to approximately the edge of the posterior surface of the femur 40. The inferior/superior length of region 39 may be 0 mm, or may extend from the lesser trochanter 740 to the superior border of the posterior surface of the femur 40.

The surfaces 37, 38, 39, which are to be mated or indexed by the tool index surfaces 101, 102, 103 of the mating region 20 of the tool 5, may be separated by areas of non-mating surfaces 110, 111 that are spanned by overestimated or non-contacting surfaces 22, 24 of the mating region 20 of the tool 5. The non-contacting surfaces 22, 24 of the mating region 20 of the tool 5 do not contact the corresponding non-mating surfaces 110, 111 of the femur 40 and may be generated via an over-estimating process during image segmentation. The non-mating surfaces 110, 111 of the proximal femur 40 may be portions 111 of the trochanteric fossa 118 (i.e., the depression between the greater trochanter and the femur neck) and portions 110 of the intertrochanteric crest 116. More specifically, the non-mating surface or portion 111 may span portions of the trochanteric fossa 118, and may have a medial boundary that is the mating surface 37 and a lateral boundary that is the mating surface 38, and a medial-lateral width that may vary between approximately 0 mm and approximately 20 mm. Non-mating surface or portion 110 may be a band including the intertrochanteric crest 116, and may extend from the lesser trochanter 740 to the most superior point of the greater trochanter 115. The medial-lateral width of the surface 110 may be from approximately 0 mm to approximately 12 mm. Generally, any surface of mating region 20 that is outside of tool mating surfaces 101, 102, 103 (which correspond to femur mating surfaces 37, 38, 39, respectively) may be tool non-contacting surfaces 22, 24, which correspond, respectively to femur non-contacting surfaces 110,111.

As can be understood from FIG. 15, the tool may be placed on the femur 40 such that the mating region 20 of the tool 5 covers and matingly receives the femur area encompassing the mating surfaces 37, 38, 39 and non-mating surfaces 110, 111 of the proximal femur 40. As discussed above, non-mating regions 110, 111, including portions of the trochanteric fossa 118 (the depression between the greater trochanter and the neck of femur) and the intertrochanteric crest 116, are not easily estimated due to drastic changes in surface geometry, and corresponding non-mating surfaces 22, 24 of the mating region 20 of the tool 5 do not contact these surfaces 110, 111 when the region of the femur that includes the femur mating surfaces 37, 38, 39 and non-mating surfaces 22, 24 are matingly received by the mating region 20 of the tool 5.

Figure 16A:
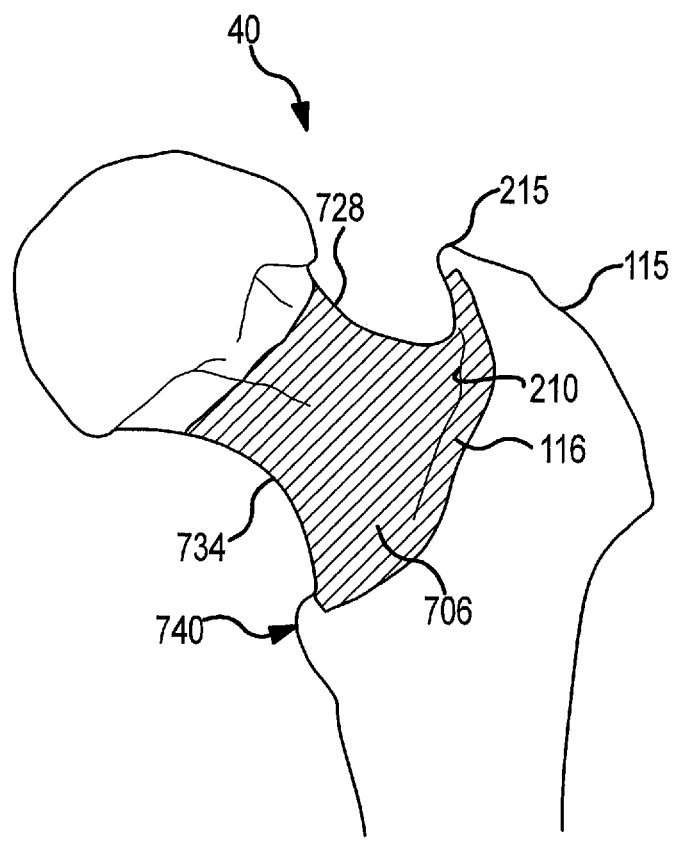
FIGS. 16A-16B are, respectively, posterior and anterior views of the proximal femur, wherein the mating region of the femur may be appropriate for a posterior or anteriorlateral surgical approach.
Figure 16B:
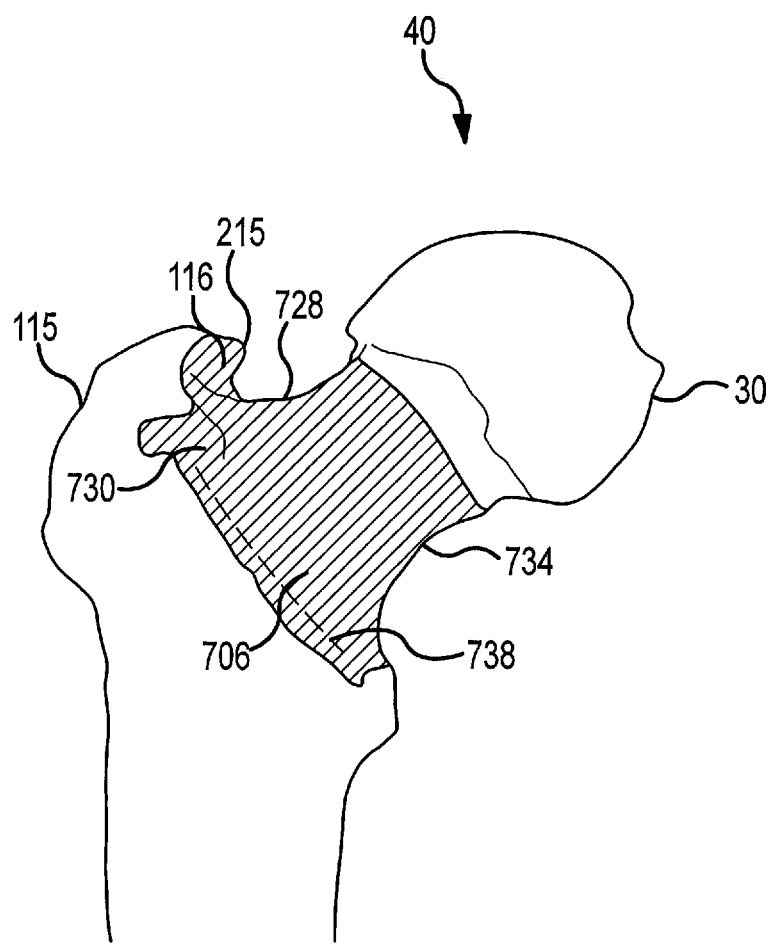

In other embodiments, as shown in FIGS. 16A-16B, the mating region of the femur 40 may be configured for use with any surgical approach, and, in a manner similar to that discussed above with respect to FIGS. 2G-2H and 13 and FIGS. 2I and 14A-14B, the tool mating region 20 may be configured to matingly engage the mating region of the femur 40 as depicted in FIGS. 16A-16B. As illustrated in FIGS. 16A-16B, a first mating surface 706 of the femur 40 may include the entire or any portion of the circumferential surface 734 of the neck 35. On the posterior surface, the mating surface 706 may start medially between approximately 1 mm and approximately 5 mm after the cartilage covering the head 30 of the femur 40 terminates laterally and extend laterally up to approximately 8 mm past the intertrochanteric crest 116, extending along the intertrochanteric crest 116 from the lesser trochanter 740 to or towards the tip 215 of the greater trochanter 115. On the anterior surface, the mating surface 706 may start medially between approximately 1 mm and approximately 5 mm after the cartilage covering the head 30 of the femur 40 terminates laterally and extend laterally up to approximately 8 mm laterally past the intertrochanteric line 738. The surface 706 may also contain the medial surface of the greater trochanter 115. As discussed above, portions within the mating surface 706 may be overestimated if geometry is too erratic for the surface to be accurately captured with the CT scan. Some such areas may include the trochanteric fossa 210, the superior junction 728 between the posterior and anterior surfaces of the neck 35, and the tubercle 730.

As can be understood from the preceding discussion regarding FIGS. 13-16B, the configuration of the mating region 20 of the tool 5 may be determined from and correspond to the specific surface geometry or topography of the surface of the femur 40 that corresponds to the surgical approach for which the tool 5 is being designed. Thus, in some embodiments, the tool mating region 20 may be configured to have the contact and non-contact surfaces that correspond to at least some, if not all, of the contact and non-contact surfaces of the femur mating region discussed above with respect to FIG. 13. In other embodiments, the tool mating region 20 may be configured to have the contact and non-contact surfaces that correspond to at least some, if not all, of the contact and non-contact surfaces of the femur mating region discussed above with respect to FIGS. 14A-14B. In yet other embodiments, the tool mating region 20 may be configured to have the contact and non-contact surfaces that correspond to at least some, if not all, of the contact and non-contact surfaces of the femur mating region discussed above with respect to FIG. 15. In still other embodiments, the tool mating region 20 may be configured to have the contact and non-contact surfaces that correspond to at least some, if not all, of the contact and non-contact surfaces of the femur mating region discussed above with respect to FIGS. 16A-16B. Thus, regardless of the surgical approach used and the mating region of the femur 40 encountered, the tool mating region 20 may be based off of the medical imaging scans take of the femur 40 and preoperatively planned via 3D computer generated models to have a customized engagement with the femur 40 when applied to the femur to guide a resection in a THR. The arrangement between the customized mating region 20 of the tool 5 and the saw guide 1725 may be such that when the mating region 20 matingly receives the mating region of the femur 40, the saw guide 1725 may cause a resection procedure guided by the guide 1725 to create a preoperatively planned resection of the femur 40.

While the above disclosed embodiments of a arthroplasty tool 5 or surgical guide tool 5 are described in the context of a tool 5 for use in a total hip replacement procedure, the features, methods of determining proper placement of the prosthetic device and the mating surfaces and the generation thereof disclosed herein may be equally useful and applicable for use in total arthroplasty procedures in other joint contexts. Thus, the disclosure provided herein should be considered as encompassing tools and the generation thereof for any total arthroplasty procedures.

Although the present invention has been described with reference to preferred embodiments, persons skilled in the art will recognize that changes may be made in form and detail without departing from the spirit and scope of the invention.

What is claimed is:

1. A method of preparing a proximal femur of a patient for implantation of a femoral implant as part of a total hip arthroplasty procedure, the method comprising:
   a) preoperatively planning the total hip arthroplasty procedure on the proximal femur of the patient, the preoperative planning including:
      i) causing a first center and a second center to positionally correspond in a computer coordinate system, wherein the first center is a center of a femoral head of a three dimensional computer model of the proximal femur and the second center is a center of a femoral head of a three dimensional computer model of the femoral implant; and
      ii) computer defining a resection of the proximal femur in the computer coordinate system when the first and second centers positionally correspond in the computer coordinate system; and
   b) resecting the proximal femur of the patient according to the computer defined resection.

2. The method of claim 1, wherein preoperative planning the total hip arthroplasty further includes coaxially aligning in the computer coordinate system a shaft of the three dimensional computer model of the femoral implant with a medullary canal or central axis of a shaft of the three dimensional computer model of the proximal femur.

3. The method of claim 1, wherein computer defining the resection of the proximal femur includes defining the resection to correspond to a location of a spacer region of the three dimensional computer model of the femoral implant when the first and second centers positionally correspond in the computer coordinate system.

4. The method of claim 1, further comprising physically registering the computer defined resection of the proximal femur with the proximal femur of the patient.

5. The method of claim 4, further comprising computer defining a registration location on a surface of the three dimensional computer model of the proximal femur; and computer referencing the computer defined resection of the proximal femur to the computer defined registration location.

6. The method of claim 5, wherein physically registering the computer defined resection of the proximal femur with the proximal femur of the patient further includes: physically contacting the proximal femur of the patient at a location on a surface of the proximal femur of the patient that corresponds to the computer defined registration location on the surface of the three dimensional computer model of the proximal femur.

7. The method of claim 6, wherein physically contacting the proximal femur of the patient includes: causing a custom mating region of a jig to matingly contact the proximal femur of the patient at the location on the surface of the proximal femur of the patient that corresponds to the computer defined registration location on the surface of the three dimensional computer model of the proximal femur.

8. The method of claim 5, wherein the computer defined registration location is on at least on a posterior neck of the three dimensional computer model of the proximal femur.

9. The method of claim 5, wherein the computer defined registration location is on at least on a posterior neck of the three dimensional computer model of the proximal femur and a posterior greater trochanter of the three dimensional computer model of the proximal femur.

10. The method of claim 9, wherein the computer defined registration location is not on a trochanteric fossa of the three dimensional computer model of the proximal femur.

11. The method of claim 9, wherein the computer defined registration location is also at least on a posterior intertrochanteric crest of the three dimensional computer model of the proximal femur.

12. The method of claim 5, wherein the computer defined registration location is at least on a posterior greater trochanter of the three dimensional computer model of the proximal femur.

13. The method of claim 12, wherein the computer defined registration location on the posterior greater trochanter of the three dimensional computer model of the proximal femur includes a portion laterally adjacent a posterior intertrochanteric crest of the three dimensional computer model of the proximal femur.

14. The method of claim 5, wherein the computer defined registration location is on at least on an anterior neck of the three dimensional computer model of the proximal femur.

15. The method of claim 14, wherein the computer defined registration location is not on a superior junction between a posterior and anterior surface of a neck of the three dimensional computer model of the proximal femur.

16. The method of claim 14, wherein the computer defined registration location is not on an inferior junction between a posterior and anterior surface of a neck of the three dimensional computer model of the proximal femur.

17. The method of claim 5, wherein the computer defined registration location is on at least on an anterior neck of the three dimensional computer model of the proximal femur and an anterior greater trochanter of the three dimensional computer model of the proximal femur.

18. The method of claim 17, wherein the computer defined registration location is not on a tubercle of the three dimensional computer model of the proximal femur.

19. The method of claim 5, wherein the computer defined registration location is at least on an anterior greater trochanter of the three dimensional computer model of the proximal femur.

20. The method of claim 19, wherein the computer defined registration location on the anterior greater trochanter of the three dimensional computer model of the proximal femur includes a portion lateral to a tubercle of the three dimensional computer model of the proximal femur.

* * * * *